(12) United States Patent
Peterson et al.

(10) Patent No.: US 7,671,093 B2
(45) Date of Patent: *Mar. 2, 2010

(54) MIXED CO-CRYSTALS AND PHARMACEUTICAL COMPOSITIONS COMPRISING THE SAME

(75) Inventors: Matthew Peterson, Hopkinton, MA (US); Magali Bourghol Hickey, Medford, MA (US); Mark Oliveira, Framingham, MA (US); Örn Almarsson, Shrewsbury, MA (US); Julius Remenar, Framingham, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 575 days.

This patent is subject to a terminal disclaimer.

(21) Appl. No.: 11/139,245

(22) Filed: May 27, 2005

(65) Prior Publication Data
US 2005/0267209 A1    Dec. 1, 2005

Related U.S. Application Data

(60) Provisional application No. 60/575,247, filed on May 28, 2004.

(51) Int. Cl.
*A61K 31/165*    (2006.01)
(52) U.S. Cl. .................................................... 514/618
(58) Field of Classification Search .................. 514/618
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,366,738 | A | 11/1994 | Rork et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,365,185 | B1 | 4/2002 | Ritschel et al. |
| 2003/0236236 | A1 | 12/2003 | Chen et al. |
| 2005/0095294 | A1 | 5/2005 | Parikh et al. |
| 2007/0026078 | A1 | 2/2007 | Almarsson et al. |

FOREIGN PATENT DOCUMENTS

| WO | 2004/014846 | 2/2004 |
| WO | 2004/026235 | 4/2004 |
| WO | 2004/078161 | 9/2004 |
| WO | 2005/023198 | 3/2005 |

OTHER PUBLICATIONS

Gavezzotti, Acc. Chem. Res. (1994), vol. 27, pp. 309-314.*
Fleischman et al., Crystal Growth and Design (2003), vol. 3(6), pp. 909-919.*
Remenar et al., J. Am. Chem. Soc. (2003), vol. 125(28), pp. 8456-8457.*
Acta Crystallographica, 1999, B55, pp. 1099-1108.
Callaghan et al., "Equilibrium moisture content of pharmaceutical excipients", Api Dev. Ind. Pharm., vol. 8, pp. 335-369 (1982).
Supplementary European Search Report re: EP 05754106 dated Aug. 6, 2009.

* cited by examiner

*Primary Examiner*—Taofiq A Solola

(57) ABSTRACT

A mixed co-crystal comprising an API, a first co-crystal former, and a second co-crystal former which is isomorphically substitutable with said first co-crystal former is described. A pharmaceutical composition comprising a mixed co-crystal, methods of making mixed co-crystals, and methods of using mixed co-crystals are also described.

2 Claims, 28 Drawing Sheets

MIXED CO-CRYSTALS AND PHARMACEUTICAL COMPOSITIONS COMPRISING THE SAME

CROSS-REFERENCE TO RELATED APPLICATIONS

The present application claims the benefit of priority of U.S. Provisional Application Ser. No. 60/575,247, filed May 28, 2004, the contents of which are incorporated herein by reference in their entirety.

FIELD OF THE INVENTION

The present invention relates to co-crystal API-containing compositions, pharmaceutical compositions comprising such APIs, and methods for preparing the same.

BACKGROUND OF THE INVENTION

Active pharmaceutical ingredients (API or APIs (plural)) in pharmaceutical compositions can be prepared in a variety of different forms. Such APIs can be prepared so as to have a variety of different chemical forms including chemical derivatives or salts. Such APIs can also be prepared to have different physical forms. For example, the APIs may be amorphous, may have different crystalline polymorphs, or may exist in different solvation or hydration states. By varying the form of an API, it is possible to vary the physical properties thereof. For example, crystalline polymorphs typically have different solubility's from one another, such that a more thermodynamically stable polymorph is less soluble than a less thermodynamically stable polymorph. Pharmaceutical polymorphs can also differ in properties such as shelf-life, bioavailability, morphology, vapour pressure, density, color, and compressibility. Accordingly, variation of the crystalline state of an API is one of many ways in which to modulate the physical properties thereof.

It would be advantageous to have new forms of these APIs that have improved properties, in particular, as oral formulations. Specifically, it is desirable to identify improved forms of APIs that exhibit significantly improved properties including increased aqueous solubility and stability. Further, it is desirable to improve the processability, or preparation of pharmaceutical formulations. For example, needle-like crystal forms or habits of APIs can cause aggregation, even in compositions where the API is mixed with other substances, such that a non-uniform mixture is obtained. It is also desirable to increase the dissolution rate of API-containing pharmaceutical compositions in water, increase the bioavailability of orally-administered compositions, and provide a more rapid onset to therapeutic effect. It is also desirable to have a form of the API which, when administered to a subject, reaches a peak plasma level faster, has a longer lasting therapeutic plasma concentration, and higher overall exposure when compared to equivalent amounts of the API in its presently-known form.

SUMMARY OF THE INVENTION

In a first embodiment, the present invention provides a mixed co-crystal, comprising:
  (a) an API;
  (b) a first co-crystal former; and
  (c) a second co-crystal former which is isomorphically substitutable with said first co-crystal former.

In another embodiment, the present invention provides a mixed co-crystal, wherein the co-crystal can be represented by the formula: $[API]_2[CCF_1]_{1-X}[CCF_2]_X$, where $0 \leq X \leq 1$. In another embodiment, the present invention provides a mixed co-crystal, wherein the co-crystal can be represented by the formula: $[API]_1[CCF_1]_{1-X}[CCF_2]_X$ where $0 \leq X \leq 1$. In another embodiment, the present invention provides a mixed co-crystal, wherein the co-crystal can be represented by the formula: $[API]_Y[CCF_1]_{1-X}[CCF_2]_X$ where $0 \leq X \leq 1$ and Y is a positive nonzero integer. In another embodiment, the present invention provides a mixed co-crystal, wherein the co-crystal can be represented by the formula: $[API]_1[CCF_1]_{2-X}[CCF_2]_X$ where $0 \leq X \leq 2$. In another embodiment, the present invention provides a mixed co-crystal, wherein the co-crystal can be represented by the formula: $[API]_2[CCF_1]_{3-X}[CCF_2]_X$ where $0 \leq X \leq 3$. In another embodiment, the present invention provides a mixed co-crystal, wherein the co-crystal can be represented by the formula: $[API]_3[CCF_1]_{2-X}[CCF_2]_X$ where $0 \leq X \leq 2$. In another embodiment, the present invention provides a mixed co-crystal, wherein the co-crystal further comprises a third co-crystal former which is isomorphically substitutable with said first co-crystal former.

In another embodiment, the present invention provides a mixed co-crystal, wherein the first and second co-crystal formers are selected from the group consisting of: acetohydroxamic acid, glycolic acid, and glycine. In another embodiment, the present invention provides a mixed co-crystal, wherein the first and second co-crystal formers are selected from the group consisting of: oxalic acid and alanine. In another embodiment, the present invention provides a mixed co-crystal, wherein the first and second co-crystal formers are selected from the group consisting of: cysteine, dimethylglycine, and serine. In another embodiment, the present invention provides a mixed co-crystal, wherein the first and second co-crystal formers are selected from the group consisting of: threonine and valine. In another embodiment, the present invention provides a mixed co-crystal, wherein the first and second co-crystal formers are selected from the group consisting of: asparagine, aspartic acid, leucine, malic acid, succinic acid, tartaric acid, isoleucine, fumaric acid, and maleic acid. In another embodiment, the present invention provides a mixed co-crystal, wherein the first and second co-crystal formers are selected from the group consisting of: lysine, arginine, xylitol, glucuronic acid, glutamic acid, N-methyl glucamine, glutamine, glutaric acid, galactaric acid, and gluconic acid. In another embodiment, the present invention provides a mixed co-crystal, wherein the first and second co-crystal formers are selected from the group consisting of: citric acid and tris. In another embodiment, the present invention provides a mixed co-crystal, wherein the first and second co-crystal formers are selected from the group consisting of: 1-hydroxy-2-naphthoic acid and vitamin K5. In another embodiment, the present invention provides a mixed co-crystal, wherein the first and second co-crystal formers are selected from the group consisting of: adenine, saccharin, allopurinol, and caffeine. In another embodiment, the present invention provides a mixed co-crystal, wherein the first and second co-crystal formers are selected from the group consisting of: chrysin, genistein, quercetin, and ipriflavone. In another embodiment, the present invention provides a mixed co-crystal, wherein the first and second co-crystal formers are selected from the group consisting of: tryptophan and clemizole. In another embodiment, the present invention provides a mixed co-crystal, wherein the first and second co-crystal formers are selected from the group consisting of: 4-aminopyridine, benzoic acid, mandelic acid, nicotinamide, nicotinic acid, benzenesulfonic acid, and benzamide. In another embodiment, the present invention provides a mixed co-crystal, wherein the first and second co-crystal formers are selected from the group consisting of: p-toluenesulfonic acid, 4-aminobenzoic acid, 4-chlorobenzenesulfonic acid, hydroquinone, 4-ethoxyphenyl urea, and salicylic acid. In another embodiment, the present invention provides a mixed co-crystal, wherein the first and second co-crystal formers are selected from the group consisting of: pyridoxamine and pyridoxine. In another embodiment, the present invention provides a mixed co-crystal, wherein the first and second co-crystal formers are selected from the group consisting of: gentisic acid and 4-aminosalicylic acid. In another embodiment, the present invention provides a mixed co-crystal, wherein the first and second co-crystal formers are selected from the group consisting of: orotic acid and ascorbic acid. In another embodiment, the present invention provides a mixed co-crystal, wherein the first and second co-crystal formers are selected from the group consisting of: phenylalanine, tyrosine, cinnamic acid, hippuric acid, procaine, resveratrol, and tryptophan. In another embodiment, the present invention provides a mixed co-crystal, wherein the first and second co-crystal formers are selected from the group consisting of: succinic acid, fumaric acid, malic acid, and tartaric acid. In another embodiment, the present invention provides a mixed co-crystal, wherein the first and second co-crystal formers are selected from the group consisting of: 5-fluorouracil and uracil.

In another embodiment, the present invention provides a mixed co-crystal, wherein the first and second co-crystal formers are enantiomers.

In another embodiment, the present invention provides a mixed co-crystal, wherein the first and second co-crystal formers are distributed homogeneously throughout the co-crystal.

In another embodiment, the present invention provides a mixed co-crystal, wherein the first and second co-crystal formers are present in equimolar amounts.

In another embodiment, the present invention provides a mixed co-crystal, wherein the first co-crystal former is present in a higher molar amount than the second co-crystal former.

In another embodiment, the present invention provides a mixed co-crystal, wherein the second co-crystal former is present in a higher molar amount than the first co-crystal former.

In another embodiment, the present invention provides a mixed co-crystal, wherein the co-crystal exhibits one endotherm as detected via differential scanning calorimetry.

In another embodiment, the present invention provides a mixed co-crystal, wherein the mixed co-crystal exhibits a shift in the 2-theta angle of at least one PXRD peak with respect to that of a parent co-crystal. In another embodiment, the present invention provides a mixed co-crystal, wherein the mixed co-crystal exhibits at least one new PXRD peak in the PXRD diffractogram with respect to that of a parent co-crystal. In another embodiment, the present invention provides a mixed co-crystal, wherein the mixed co-crystal exhibits loss of at least one PXRD peak in the PXRD diffractogram with respect to that of a parent co-crystal.

In another embodiment, the present invention provides a mixed co-crystal, wherein its melting point is intermediate to all parent co-crystals. In another embodiment, the present invention provides a mixed co-crystal, wherein its solubility is intermediate to all parent co-crystals. In another embodiment, the present invention provides a mixed co-crystal, wherein its dissolution is intermediate to all parent co-crystals. In another embodiment, the present invention provides a mixed co-crystal, wherein its bioavailability is intermediate to all parent co-crystals.

In another embodiment, the present invention provides a mixed co-crystal, wherein the API is modafinil, the first co-crystal former is succinic acid, and the second co-crystal former is fumaric acid.

In another embodiment, the present invention provides a mixed co-crystal, wherein the co-crystal can be represented by the formula: $[API]_2[CCF_1]_{0.9}[CCF_2]_{0.1}$.

In another embodiment, the present invention provides a mixed co-crystal, wherein the co-crystal can be represented by the formula: $[API]_2[CCF_1]_{0.8}[CCF_2]_{0.2}$.

In another embodiment, the present invention provides a mixed co-crystal, wherein the co-crystal can be represented by the formula: $[API]_2[CCF_1]_{0.7}[CCF_2]_{0.3}$.

In another embodiment, the present invention provides a mixed co-crystal, wherein the co-crystal can be represented by the formula: $[API]_2[CCF_1]_{0.6}[CCF_2]_{0.4}$.

In another embodiment, the present invention provides a mixed co-crystal, wherein the co-crystal can be represented by the formula: $[API]_2[CCF_1]_{0.5}[CCF_2]_{0.5}$.

In another embodiment, the present invention provides a mixed co-crystal, wherein the co-crystal can be represented by the formula: $[API]_2[CCF_1]_{0.4}[CCF_2]_{0.6}$.

In another embodiment, the present invention provides a mixed co-crystal, wherein the co-crystal can be represented by the formula: $[API]_2[CCF_1]_{0.3}[CCF_2]_{0.7}$.

In another embodiment, the present invention provides a mixed co-crystal, wherein the co-crystal can be represented by the formula: $[API]_2[CCF_1]_{0.2}[CCF_2]_{0.8}$.

In another embodiment, the present invention provides a mixed co-crystal, wherein the co-crystal can be represented by the formula: $[API]_2[CCF_1]_{0.1}[CCF_2]_{0.9}$.

In another embodiment, the present invention provides a mixed co-crystal, wherein the API is urea, the first co-crystal former is 5-fluorouracil, and the second co-crystal former is uracil.

In another embodiment, the present invention provides a mixed co-crystal, wherein the co-crystal can be represented by the formula: $[API]_1[CCF_1]_{0.9}[CCF_2]_{0.1}$.

In another embodiment, the present invention provides a mixed co-crystal, wherein the co-crystal can be represented by the formula: $[API]_1[CCF_1]_{0.8}[CCF_2]_{0.2}$.

In another embodiment, the present invention provides a mixed co-crystal, wherein the co-crystal can be represented by the formula: $[API]_1[CCF_1]_{0.7}[CCF_2]_{0.3}$.

In another embodiment, the present invention provides a mixed co-crystal, wherein the co-crystal can be represented by the formula: $[API]_1[CCF_1]_{0.6}[CCF_2]_{0.4}$.

In another embodiment, the present invention provides a mixed co-crystal, wherein the co-crystal can be represented by the formula: $[API]_1[CCF_1]_{0.5}[CCF_2]_{0.5}$.

In another embodiment, the present invention provides a mixed co-crystal, wherein the co-crystal can be represented by the formula: $[API]_1[CCF_1]_{0.4}[CCF_2]_{0.6}$.

In another embodiment, the present invention provides a mixed co-crystal, wherein the co-crystal can be represented by the formula: $[API]_1[CCF_1]_{0.3}[CCF_2]_{0.7}$.

In another embodiment, the present invention provides a mixed co-crystal, wherein the co-crystal can be represented by the formula: $[API]_1[CCF_1]_{0.2}[CCF_2]_{0.8}$.

In another embodiment, the present invention provides a mixed co-crystal, wherein the co-crystal can be represented by the formula: $[API]_1[CCF_1]_{0.1}[CCF_2]_{0.9}$.

In another embodiment, the present invention provides a pharmaceutical composition comprising a mixed co-crystal.

In another embodiment, the present invention provides a pharmaceutical composition, further comprising a diluent, excipient, or carrier.

In another embodiment, the present invention provides a method of making a mixed co-crystal, comprising:
(a) providing an API;
(b) providing a first co-crystal former;
(c) providing a second co-crystal former which is isostructural with said first co-crystal former;
(d) grinding, heating, co-subliming, co-melting, or contacting in solution the API with the first and second co-crystal formers under crystallization conditions so as to form a solid phase; and
(e) optionally isolating the mixed co-crystal formed thereby.

In another embodiment, the present invention provides a method for modulating a chemical or physical property of interest of a solid, comprising: preparing a mixed co-crystal comprising an API and two or more isomorphically substitutable co-crystal formers.

In another embodiment, the present invention provides a method for modulating a chemical or physical property of interest of a mixed co-crystal, comprising:
(a) measuring the chemical or physical property of interest for each parent co-crystal;
(b) determining the mole fraction of each co-crystal former that will result in the desired modulation of the chemical or physical property of interest; and
(c) preparing the mixed co-crystal with the mole fraction of each co-crystal former determined in step (b).

In another embodiment, the present invention provides a method of using a mixed co-crystal, comprising administering said mixed co-crystal to a mammal in need of a therapeutic effect.

In another embodiment, the present invention provides a medicament comprising a mixed co-crystal. In another embodiment, the present invention provides a medicament, further comprising a diluent, excipient, or carrier.

DETAILED DESCRIPTION OF THE INVENTION

Figure 1:
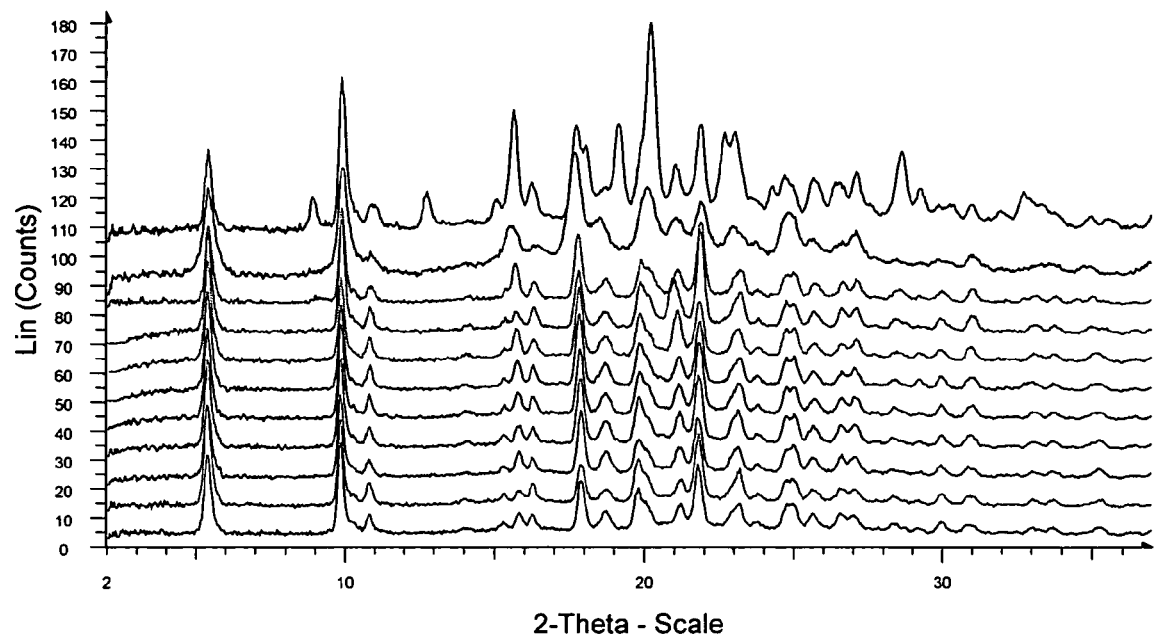
FIG. 1 shows an overlay of 11 PXRD diffractograms of the modafinil:succinic acid co-crystal, the modafinil:fumaric acid co-crystal, and nine mixed co-crystals (0.1-0.9 fumaric acid mole fraction, in increments of 0.1)

The term "co-crystal" as used herein means a crystalline material comprised of two or more unique solids at room temperature, each containing distinctive physical characteristics, such as structure, melting point and heats of fusion, with the exception that, if specifically stated, the API (active pharmaceutical ingredient) may be a liquid at room temperature. The co-crystals of the present invention comprise a co-crystal former H-bonded to an API. The co-crystal former may be H-bonded directly to the API or may be H-bonded to an additional molecule which is bound to the API. The additional molecule may be H-bonded to the API or bound ionically or covalently to the API. The additional molecule could also be a different API. Solvates of API compounds that do not further comprise a co-crystal forming compound are not co-crystals according to the present invention. The co-crystals may however, include one or more solvate molecules in the crystalline lattice. That is, solvates of co-crystals, or a co-crystal further comprising a solvent or compound that is a liquid at room temperature, is included in the present invention, but crystalline material comprised of only one solid and one or more liquids (at room temperature) are not included in the present invention, with the previously noted exception of specifically stated liquid APIs. The co-crystals may also be a co-crystal between a co-crystal former and a salt of an API, but the API and the co-crystal former of the present invention are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads. An alternative embodiment provides for a co-crystal wherein the co-crystal former is a second API. In another embodiment, the co-crystal former is not an API. In another embodiment the co-crystal comprises two co-crystal formers. Co-crystals may also be formed where the API is a "guest" molecule in regions of a crystalline lattice formed by the co-crystal forming compound, thus forming an inclusion complex. For purposes of the present invention, the chemical and physical properties of an API in the form of a co-crystal may be compared to a reference compound that is the same API in a different form. The reference compound may be specified as a free form, or more specifically, a free acid, free base, or zwitter ion; a salt, or more specifically for example, an inorganic base addition salt such as sodium, potassium, lithium, calcium, magnesium, ammonium, aluminum salts or organic base addition salts, or an inorganic acid addition salts such as HBr, HCl, sulfuric, nitric, or phosphoric acid addition salts or an organic acid addition salt such as acetic, proprionic, pyruvic, malonic, succinic, malic, maleic, fumaric, tartaric, citric, benzoic, methanesulfonic, ethanesulforic, stearic or lactic acid addition salt; an anhydrate or hydrate of a free form or salt, or more specifically, for example, a hemihydrate, monohydrate, dihydrate, trihydrate, quadrahydrate, pentahydrate; or a solvate of a free form or salt. The reference compound may also be specified as crystalline or amorphous.

The term "pharmaceutical co-crystal" can be used to specify a co-crystal where at least one of the components is an API. The term "co-crystal" is a broader term which encompasses both API-containing and non-API-containing co-crystals. As such, API-containing co-crystals can be termed either "co-crystals" or "pharmaceutical co-crystals" according to the present invention.

According to the present invention, the co-crystals can include an acid addition salt or base addition salt of an API. Acid addition salts include, but are not limited to, inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid. Base addition salts include, but are not limited to, inorganic bases such as sodium, potassium, lithium, ammonium, calcium and magnesium salts, and organic bases such as primary, secondary and tertiary amines (e.g. isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, and N-ethylpiperidine).

The ratio of API to co-crystal former may be stoichiometric or non-stoichiometric according to the present invention. For example, 1:1, 1:1.5 and 1:2 ratios of API:co-crystal former are acceptable.

It has surprisingly been found that when an API and a selected co-crystal forming compound are allowed to form co-crystals, the resulting co-crystals give rise to improved properties of the API, as compared to the API in a free form (including free acids, free bases, and zwitter ions, hydrates, solvates, etc.), or an acid or base salt thereof particularly with respect to: solubility, dissolution, bioavailability, stability, Cmax, Tmax, processability, longer lasting therapeutic plasma concentration, hygroscopicity, crystallization of amorphous compounds, decrease in form diversity (including polymorphism and crystal habit), change in morphology or crystal habit, etc. For example, a co-crystal form of an API is particularly advantageous where the original API is insoluble or sparingly soluble in water. Additionally, the co-crystal properties conferred upon the API are also useful because the bioavailability of the API can be improved and the plasma concentration and/or serum concentration of the API can be improved. This is particularly advantageous for orally-administrable formulations. Moreover, the dose response of the API can be improved, for example by increasing the maximum attainable response and/or increasing the potency of the API by increasing the biological activity per dosing equivalent.

Accordingly, in a first aspect, the present invention provides a pharmaceutical composition comprising a co-crystal of an API and a co-crystal forming compound, such that the API and co-crystal forming compound are capable of co-crystallizing from a solution phase under crystallization conditions or from the solid-state, for example, through grinding or heating. In another aspect, the API has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine and a co-crystal forming compound which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine, or a functional group in a Table herein, such that the API and co-crystal forming compound are capable of co-crystallizing from a solution phase under crystallization conditions.

The co-crystals of the present invention are formed where the API and co-crystal forming compound are bonded together through hydrogen bonds. Other non-covalent interactions, including pi-stacking and van der Waals interactions, may also be present.

In another embodiment, the difference in $pK_a$ value of the co-crystal former and the API is less than 2. In other embodiments, the difference in $pK_a$ values of the co-crystal former and API is less than 3, less than 4, less than 5, between 2 and 3, between 3 and 4, or between 4 and 5.

In another embodiment, the co-crystal comprises more than one co-crystal former. For example, two, three, four, five, or more co-crystal formers can be incorporated in a co-crystal with an API. Co-crystals which comprise two or more co-crystal formers and an API are bound together via hydrogen bonds. In one embodiment, incorporated co-crystal formers are hydrogen bonded to the API molecules. In another embodiment, co-crystal formers are hydrogen bonded to either the API molecules or the incorporated co-crystal formers.

In a further embodiment, several co-crystal formers can be contained in a single compartment, or kit, for ease in screening an API for potential co-crystal species. The co-crystal kit can comprise 1, 2, 4, 8, 16, 24, 32, 40, 48, 96, 384, 512, 1024, 1536, or more or an intermediate integer amount of the co-crystal formers in Tables I and II. The co-crystal formers are in solid form and in an array of individual reaction vials such that individual co-crystal formers can be tested with one or more APIs by one or more crystallization methods or multiple co-crystal formers can be easily tested against one or more compounds by one or more crystallization methods. The crystallization methods include, but are not limited to, melt recrystallization, grinding, milling, standing, co-crystal formation from solution by evaporation, thermally driven crystallization from solution, co-crystal formation from solution by addition of anti-solvent, co-crystal formation from solution by vapor-diffusion, co-crystal formation from solution by drown-out, co-crystal formation from solution by any combination of the above mentioned techniques, co-crystal formation by co-sublimation, co-crystal formation by sublimation using a Knudsen cell apparatus, co-crystal formation by standing the desired components of the co-crystal in the presence of solvent vapor, co-crystal formation by slurry conversion of the desired components of the co-crystal in a solvent or mixtures of solvents, or co-crystal formation by any combination of the above techniques in the presence of additives, nucleates, crystallization enhancers, precipitants, chemical stabilizers, or anti-oxidants. The co-crystallization kits can be used alone or as part of larger crystallization experiments. For example, kits can be constructed as single co-crystal former single well kits, single co-crystal former multi-well kits, multi-co-crystal former single well kits, or multi-co-crystal former multi-well kits.

In a further embodiment, the API is selected from an API of Table IV of U.S. application Ser. No. 10/660,202, filed Sep. 11, 2003. In further embodiments, the functional group of the particular API interacting with the co-crystal former is specified. A specific functional group of a co-crystal former, a specific co-crystal former, or a specified functional group or a specific co-crystal former interacting with the particular API may also be specified.

In each process according to the invention, there is a need to contact the API with the co-crystal forming compound. This may involve grinding the two solids together or melting one or both components and allowing them to recrystallize. This may also involve either solubilizing the API and adding the co-crystal forming compound, or solubilizing the co-crystal forming compound and adding the API. Crystallization conditions are applied to the API and co-crystal forming compound. This may entail altering a property of the solution, such as pH or temperature and may require concentration of the solute, usually by removal of the solvent, typically by drying the solution. Solvent removal results in the concentration of both API and co-crystal former increasing over time so as to facilitate crystallization. Once the solid phase comprising any crystals is formed, this may be tested as described herein.

The co-crystals obtained as a result of such process steps may be readily incorporated into a pharmaceutical composition by conventional means. Pharmaceutical compositions in general are discussed in further detail below and may further comprise a pharmaceutically-acceptable diluent, excipient or carrier.

In a further aspect, the present invention provides a process for the production of a pharmaceutical composition, which process comprises:

(1) providing an API which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile diazo, organohalide, nitro, S-heterocyclic ring, thiophene, N-heterocyclic ring, pyrrole, O-heterocyclic ring, furan, epoxide, peroxide, hydroxamic acid, imidazole, and pyridine;

(2) providing a co-crystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine;

(3) grinding, heating or contacting in solution the API with the co-crystal forming compound under crystallization conditions;

(4) isolating co-crystals formed thereby; and (5) incorporating the co-crystals into a pharmaceutical composition.

In a still further aspect the present invention provides a process for the production of a pharmaceutical composition, which comprises:

(1) grinding, heating or contacting in solution an API with a co-crystal forming compound, under crystallization conditions, so as to form a solid phase;

(2) isolating co-crystals comprising the API and the co-crystal forming compound; and (3) incorporating the co-crystals into a pharmaceutical composition.

Assaying the solid phase for the presence of co-crystals of the API and the co-crystal forming compound may be carried out by conventional methods known in the art. For example, it is convenient and routine to use powder X-ray diffraction techniques to assess the presence of co-crystals. This may be affected by comparing the spectra of the API, the crystal forming compound and putative co-crystals in order to establish whether or not true co-crystals had been formed. Other techniques, used in an analogous fashion, include differential scanning calorimetry (DSC), thermogravimetric analysis (TGA) and Raman spectroscopy. Single crystal X-ray diffraction is especially useful in identifying co-crystal structures.

In a further aspect, the present invention therefore provides a process of screening for co-crystal compounds, which comprises:
(1) providing (i) an API compound, and (ii) a co-crystal forming compound; and
(2) screening for co-crystals of APIs with co-crystal forming compounds by subjecting each combination of API and co-crystal forming compound to a step comprising:
(a) grinding, heating or contacting in solution the API with the co-crystal forming compound under crystallization conditions so as to form a solid phase; and
(b) isolating co-crystals comprising the API and the co-crystal forming compound.

An alternative embodiment is drawn to a process of screening for co-crystal compounds, which comprises:
(1) providing (i) an API or a plurality of different APIs, and (ii) a co-crystal forming compound or a plurality of different co-crystal forming compounds, wherein at least one of the API and the co-crystal forming compound is provided as a plurality thereof; and
(2) screening for co-crystals of APIs with co-crystal forming compounds by subjecting each combination of API and co-crystal forming compound to a step comprising
(a) grinding, heating or contacting in solution the API with the co-crystal forming compound under crystallization conditions so as to form a solid phase; and
(b) isolating co-crystals comprising the API and the co-crystal forming compound.

As defined herein, a mixed co-crystal is a co-crystal which comprises three or more distinct chemical entities, wherein two or more chemical entities occupy essentially the same space in the crystallographic asymmetric unit or unit cell of a co-crystal and are dispersed throughout the bulk crystal by substituting one chemical entity for the second chemical entity in a random manner. Isostructurality can be defined as sufficiently similar unit cell parameters. A high degree of internal overlap of atomic positions can also indicate isostructurality. In one embodiment, a pair of enantiomers can be considered to be isostructural. In another embodiment, isostructurality can be limited to molecules with identical atomic configurations. In another embodiment, isostructurality can be described by the expression $pi = abs[(a+b+c)/(a'+b'+c')]-1$ where pi is equal to or approaches zero (a, b, and c are unit cell parameters of one crystalline lattice, a', b', and c' are unit cell parameters of another crystalline lattice). Expression is taken from *Acta Crystallographica* 1999, B55, 1099-1108. In another embodiment, isostructurality is defined as $-0.5 \leq pi \leq 0.5$. In another embodiment, isostructurality is defined as $-0.25 \leq pi \leq 0.25$. In another embodiment, isostructurality is defined as $-0.1 \leq pi \leq 0.1$. In another embodiment, isostructurality is defined as $-0.05 \leq pi \leq 0.05$. In another embodiment, isostructurality is defined as $-0.01 \leq pi \leq 0.01$. Mixed co-crystals incorporate an isomorphous replacement of one or more co-crystal components. Isomorphous structures can vary in atomic configurations but retain the same functional group geometries and interactions. An isomorphous replacement or substitution of co-crystal formers within a co-crystalline lattice requires the same intermolecular interactions which are responsible for the overall crystal structure be present. To accomplish this, isomorphous co-crystal formers must comprise the same or similar functional groups and geometries. Therefore, the parent co-crystal structure is retained by any one of several isomorphous co-crystal formers in a subsequent mixed co-crystal. In another embodiment, isostructural co-crystal formers can be interchanged within a mixed co-crystalline lattice without changing the crystal structure. In another embodiment, isomorphous co-crystal formers can be interchanged within a mixed co-crystalline lattice without changing the crystal structure. Isomorphism can be defined as the ability to crystallize in a form similar to that of another compound, salt, or co-crystal. As a specific non-limiting example, a co-crystal comprising modafinil and succinic acid can undergo isomorphous replacement in the presence of an isostructural co-crystal former such as fumaric acid. In this case, a mixed pharmaceutical co-crystal comprising modafinil, succinic acid, and fumaric acid results where a portion of the succinic acid molecules have been replaced by fumaric acid. Generally, a non-limiting example of a mixed co-crystal is described by the expression $[API][CCF_1]_{1-X}[CCF_2]_X$, where the first co-crystal former ($CCF_1$) has undergone isomorphous replacement by a second co-crystal former ($CCF_2$). Mixed co-crystals can have any one of many stoichiometries, including, but not limited to, $[API]_2[CCF_1]_{1-X}[CCF_2]_X$ where $0 \leq X \leq 1$, $[API]_1[CCF_1]_{1-X}[CCF_2]_X$ where $0 \leq X \leq 1$, $[API]_Y[CCF_1]_{1-X}[CCF_2]_X$ where $0 \leq X \leq 1$ and Y is a positive nonzero integer, $[API]_1[CCF_1]_{2-X}[CCF_2]_X$ where $0 \leq X \leq 2$, $[API]_2[CCF_1]_{3-X}[CCF_2]_X$ where $0 \leq X \leq 3$ and $[API]_3[CCF_1]_{2-X}[CCF_2]_X$ where $0 \leq X \leq 2$. In Example 1, a mixed pharmaceutical co-crystal is described wherein the components of the co-crystal are modafinil, succinic acid, and fumaric acid. Succinic and fumaric acid are isomorphically substitutable and can be interchanged within the co-crystalline lattice without significantly altering the intermolecular structure of the co-crystal.

In another embodiment, a mixed co-crystal comprises:
(a) an API;
(b) a first co-crystal former; and
(c) a second co-crystal former which is isomorphically substitutable with said first co-crystal former.

The properties of a mixed co-crystal can be compared to that of one or more of its parent co-crystals as a reference material. A parent co-crystal is defined as a co-crystal which consists essentially of an API and only one of the co-crystal formers of the related mixed co-crystal. For example, a mixed co-crystal comprising modafinil, succinic acid, and fumaric acid has two parent co-crystals: a modafinil:succinic acid co-crystal and a modafinil:fumaric acid co-crystal.

Mixed co-crystals can comprise more than three chemical entities and can include more than two isomorphically substitutable species. In addition, such mixed co-crystals are not limited to mixed co-crystals of modafinil, but can comprise one or more of many APIs, including those listed in Table IV of U.S. application Ser. No. 10/660,202, filed Sep. 11, 2003, said Table IV is herein incorporated by reference in its entirety. Tables I, II, and III of U.S. application Ser. No. 10/660,202, filed Sep. 11, 2003, are also incorporated by reference in their entireties. Said Tables I, II, and III of said U.S. application include lists of co-crystal formers, and H-bonding functional groups (donors and acceptors) of both APIs and co-crystal formers.

In another embodiment, the co-crystal formers in a mixed co-crystal are distributed homogeneously throughout the co-crystal. The co-crystal formers can be present in equimolar amounts or in other molar amounts. For example, the mole fraction of one co-crystal former with respect to all co-crystal formers present in a mixed co-crystal can be about 0.001, 0.005, 0.01, 0.05, 0.10, 0.15, 0.20, 0.25, 0.30, 0.35, 0.40, 0.45, 0.50, 0.55, 0.60, 0.65, 0.70, 0.75, 0.80, 0.85, 0.9, 0.95, 0.99, 0.995, 0.999, or any intermediate value.

In another embodiment, a mixed co-crystal exhibits one endotherm as detected via differential scanning calorimetry (DSC). DSC can be used to characterize and distinguish mixed co-crystals from mixtures of two or more distinct co-crystals. DSC and PXRD can also be used to show homogeneity throughout the crystalline structure.

In another embodiment, the present invention provides a mixed co-crystal, wherein the mixed co-crystal exhibits a peak shift of one or more PXRD peaks with respect to the PXRD diffractogram of one or more of the parent co-crystals. In another embodiment, the present invention provides a mixed co-crystal, wherein the mixed co-crystal exhibits at least one new PXRD peak in the PXRD diffractogram with respect to that of a parent co-crystal. In another embodiment, the present invention provides a mixed co-crystal, wherein the mixed co-crystal exhibits loss of at least one PXRD peak in the PXRD diffractogram with respect to that of a parent co-crystal.

In another embodiment, a mixed co-crystal exhibits physical and chemical properties which are commensurate with those of the parent co-crystals. These physical and chemical properties include, but are not limited to, melting point, solubility, dissolution, bioavailability, hygroscopicity, etc. In another embodiment, a mixed co-crystal exhibits physical and chemical properties which depend linearly on the mixed co-crystal composition with respect to the parent co-crystals. For example, a mixed co-crystal comprising modafinil (API), succinic acid ($CCF_1$), and fumaric acid ($CCF_2$) where the stoichiometry is $[API]_2[CCF_1]_{0.9}[CCF_2]_{0.1}$ exhibits physical and chemical properties closely related to that of the parent co-crystal modafinil:succinic acid. However, a mixed co-crystal comprising modafinil (API), succinic acid ($CCF_1$), and fumaric acid ($CCF_2$) where the stoichiometry is $[API]_2[CCF_1]_{0.1}[CCF_2]_{0.9}$ exhibits physical and chemical properties closely related to that of the parent co-crystal modafinil:fumaric acid.

In another embodiment, the present invention provides a mixed co-crystal, wherein the API is modafinil, the first co-crystal former-is succinic acid, and the second co-crystal former is fumaric acid.

In another embodiment, the present invention provides a mixed co-crystal, wherein the co-crystal can be represented by the formula: $[API]_2[CCF_1]_{0.9}[CCF_2]_{0.1}$.

In another embodiment, the present invention provides a mixed co-crystal, wherein the co-crystal can be represented by the formula: $[API]_2[CCF_1]_{0.8}[CCF_2]_{0.2}$.

In another embodiment, the present invention provides a mixed co-crystal, wherein the co-crystal can be represented by the formula: $[API]_2[CCF_1]_{0.7}[CCF_2]_{0.3}$.

In another embodiment, the present invention provides a mixed co-crystal, wherein the co-crystal can be represented by the formula: $[API]_2[CCF_1]_{0.6}[CCF_2]_{0.4}$.

In another embodiment, the present invention provides a mixed co-crystal, wherein the co-crystal can be represented by the formula: $[API]_2[CCF_1]_{0.5}[CCF_2]_{0.5}$.

In another embodiment, the present invention provides a mixed co-crystal, wherein the co-crystal can be represented by the formula: $[API]_2[CCF_1]_{0.4}[CCF_2]_{0.6}$.

In another embodiment, the present invention provides a mixed co-crystal, wherein the co-crystal can be represented by the formula: $[API]_2[CCF_1]_{0.3}[CCF_2]_{0.7}$.

In another embodiment, the present invention provides a mixed co-crystal, wherein the co-crystal can be represented by the formula: $[API]_2[CCF_1]_{0.2}[CCF_2]_{0.8}$.

In another embodiment, the present invention provides a mixed co-crystal, wherein the co-crystal can be represented by the formula: $[API]_2[CCF_1]_{0.1}[CCF_2]_{0.9}$.

In another embodiment, the present invention provides a mixed co-crystal, wherein the API is urea, the first co-crystal former is 5-fluorouracil, and the second co-crystal former is uracil.

In another embodiment, the present invention provides a mixed co-crystal, wherein the co-crystal can be represented by the formula: $[API]_1[CCF_1]_{0.9}[CCF_2]_{0.1}$.

In another embodiment, the present invention provides a mixed co-crystal, wherein the co-crystal can be represented by the formula: $[API]_1[CCF_1]_{0.8}[CCF_2]_{0.2}$.

In another embodiment, the present invention provides a mixed co-crystal, wherein the co-crystal can be represented by the formula: $[API]_1[CCF_1]_{0.7}[CCF_2]_{0.3}$.

In another embodiment, the present invention provides a mixed co-crystal, wherein the co-crystal can be represented by the formula: $[API]_1[CCF_1]_{0.6}[CCF_2]_{0.4}$.

In another embodiment, the present invention provides a mixed co-crystal, wherein the co-crystal can be represented by the formula: $[API]_1[CCF_1]_{0.5}[CCF_2]_{0.5}$.

In another embodiment, the present invention provides a mixed co-crystal, wherein the co-crystal can be represented by the formula: $[API]_1[CCF_1]_{0.4}[CCF_2]_{0.6}$.

In another embodiment, the present invention provides a mixed co-crystal, wherein the co-crystal can be represented by the formula: $[API]_1[CCF_1]_{0.3}[CCF_2]_{0.7}$.

In another embodiment, the present invention provides a mixed co-crystal, wherein the co-crystal can be represented by the formula: $[API]_1[CCF_1]_{0.2}[CCF_2]_{0.8}$.

In another embodiment, the present invention provides a mixed co-crystal, wherein the co-crystal can be represented by the formula: $[API]_1[CCF_1]_{0.1}[CCF_2]_{0.9}$.

In another embodiment, the present invention provides a pharmaceutical composition comprising a mixed co-crystal. In another embodiment, the present invention provides a pharmaceutical composition, further comprising a diluent, excipient, or carrier.

In another embodiment, the present invention comprises a method for modulating a chemical or physical property of interest of a solid, comprising preparing a mixed co-crystal comprising an API and two or more co-crystal formers.

In another embodiment, the present invention comprises a method for modulating a chemical or physical property of interest of a mixed co-crystal, comprising:
  (a) measuring the chemical or physical property of interest for each parent co-crystal;
  (b) determining the mole fraction of each co-crystal former that will result in the desired modulation of the chemical or physical property of interest; and
  (c) preparing the mixed co-crystal with the mole fraction of each co-crystal former determined in step (b).

In another embodiment, the present invention provides a pharmaceutical composition comprising a mixed co-crystal. In another embodiment, the pharmaceutical composition further comprises a diluent, excipient, or carrier.

In another embodiment, the present invention comprises a method of making a mixed co-crystal, comprising:
  (a) providing an API;
  (b) providing a first co-crystal former;

(c) providing a second co-crystal former which is isomorphically substitutable with said first co-crystal former;
(d) grinding, heating, co-subliming, co-melting, or contacting in solution the API with the first and second co-crystal formers under crystallization conditions so as to form a solid phase; and
(e) optionally isolating the mixed co-crystal formed thereby.

In another embodiment, isomorphically substitutable co-crystal formers are selected from the group consisting of: acetohydroxamic acid, glycolic acid, and glycine. In another embodiment, isomorphically substitutable co-crystal formers are selected from the group consisting of: oxalic acid and alanine. In another embodiment, isomorphically substitutable co-crystal formers are selected from the group consisting of: cysteine, dimethylglycine, and serine. In another embodiment, isomorphically substitutable co-crystal formers are selected from the group consisting of: threonine and valine. In another embodiment, isomorphically substitutable co-crystal formers are selected from the group consisting of: asparagine, aspartic acid, leucine, malic acid, succinic acid, tartaric acid, isoleucine, fumaric acid, and maleic acid. In another embodiment, isomorphically substitutable co-crystal formers are selected from the group consisting of: lysine, arginine, xylitol, glucuronic acid, glutamic acid, N-methyl glucamine, glutamine, glutaric acid, galactaric acid, and gluconic acid. In another embodiment, isomorphically substitutable co-crystal formers are selected from the group consisting of: citric acid and tris. In another embodiment, isomorphically substitutable co-crystal formers are selected from the group consisting of: 1-hydroxy-2-naphthoic acid and vitamin K5. In another embodiment, isomorphically substitutable co-crystal formers are selected from the group consisting of: adenine, saccharin, allopurinol, and caffeine. In another embodiment, isomorphically substitutable co-crystal formers are selected from the group consisting of: chrysin, genistein, quercetin, and iprifavone. In another embodiment, isomorphically substitutable co-crystal formers are selected from the group consisting of: tryptophan and clemizole. In another embodiment, isomorphically substitutable co-crystal formers are selected from the group consisting of: 4-aminopyridine, benzoic acid, mandelic acid, nicotinamide, nicotinic acid, benzenesulfonic acid, and benzamide. In another embodiment, isomorphically substitutable co-crystal formers are selected from the group consisting of: p-toluenesulfonic acid, 4-aminobenzoic acid, 4-chlorobenzenesulfonic acid, hydroquinone, 4-ethoxyphenyl urea, and salicylic acid. In another embodiment, isomorphically substitutable co-crystal formers are selected from the group consisting of: pyridoxamine and pyridoxine. In another embodiment, isomorphically substitutable co-crystal formers are selected from the group consisting of: gentisic acid and 4-aminosalicylic acid. In another embodiment, isomorphically substitutable co-crystal formers are selected from the group consisting of: orotic acid and ascorbic acid. In another embodiment, isomorphically substitutable co-crystal formers are selected from the group consisting of: phenylalanine, tyrosine, cinnamic acid, hippuric acid, procaine, resveratrol, and tryptophan. In another embodiment, isomorphically substitutable co-crystal formers are selected from the group consisting of: succinic acid, fumaric acid, malic acid, and tartaric acid.

In another embodiment, mixed co-crystals comprising enantiomeric co-crystal formers can be specifically excluded from the present invention.

Figure 8:
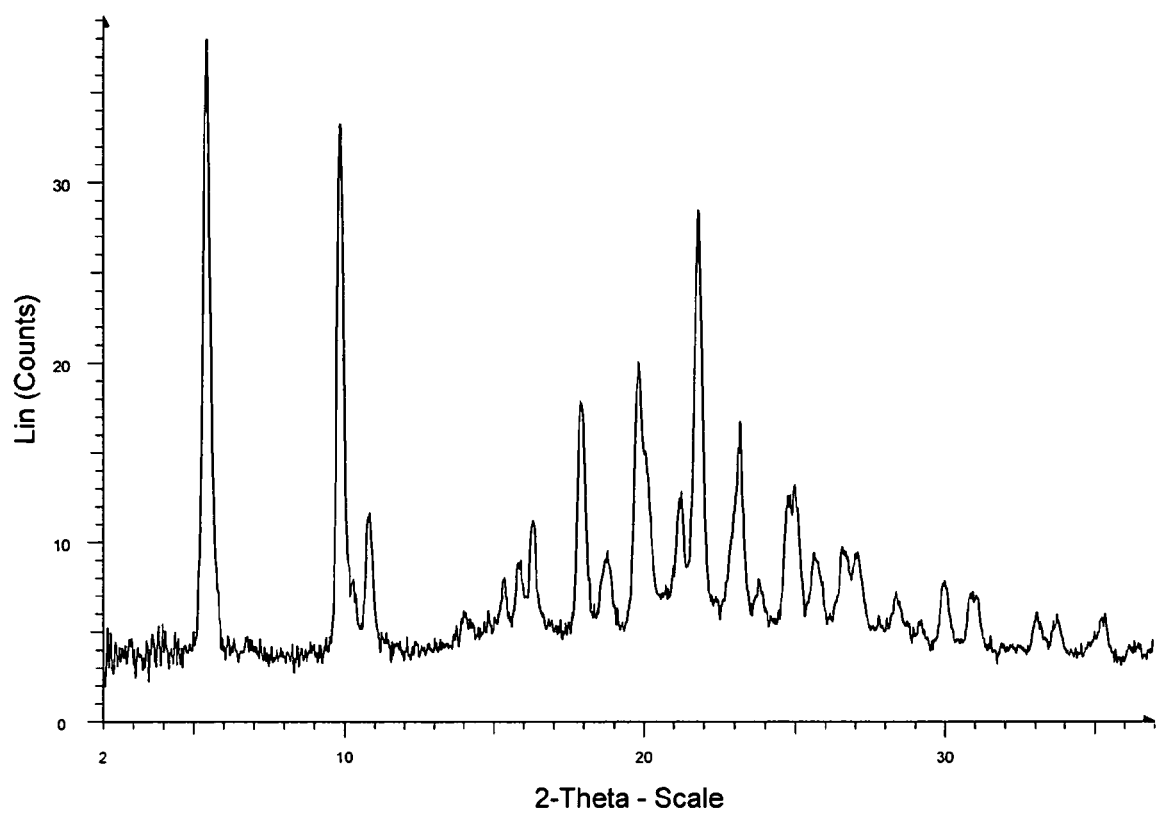
FIG. 8 shows a PXRD diffractogram of a 1:0.9:0.1 modafinil:succinic acid:fumaric acid mixed co-crystal.
Figure 9:
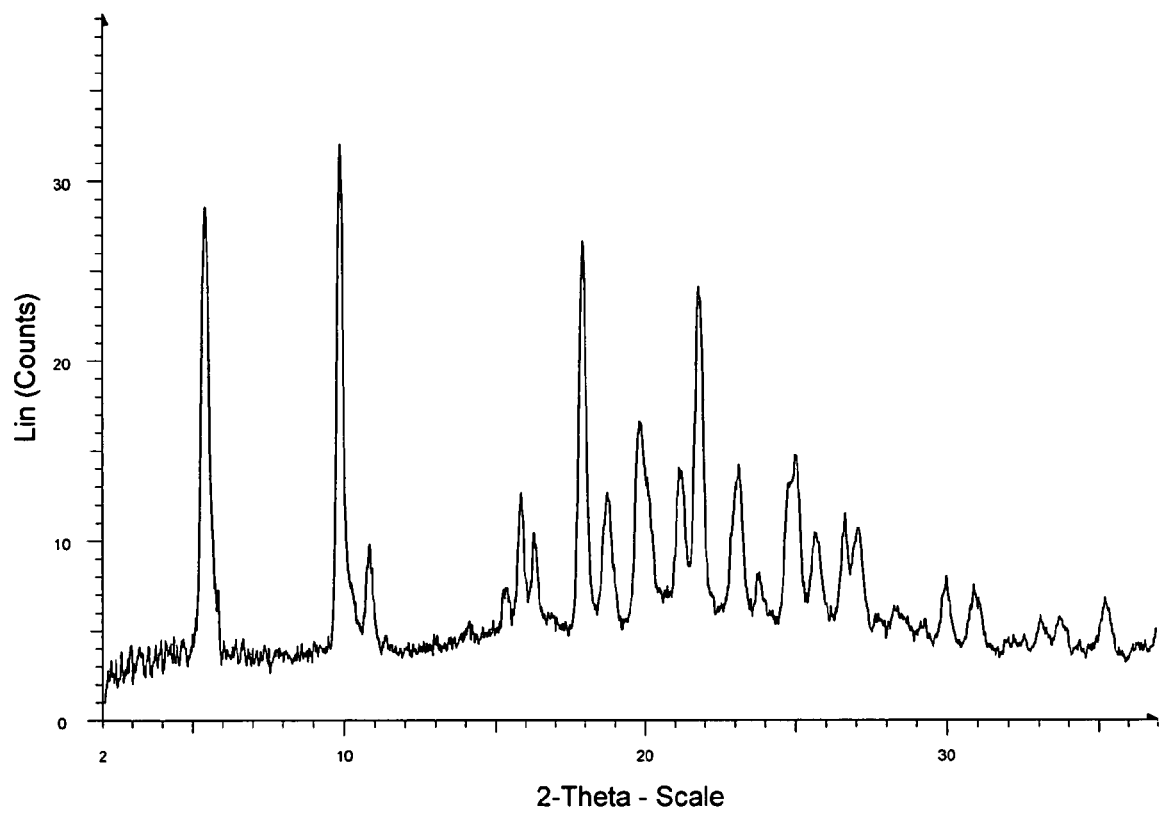
FIG. 9 shows a PXRD diffractogram of a 1:0.8:0.2 modafinil:succinic acid:fumaric acid mixed co-crystal.
Figure 10:
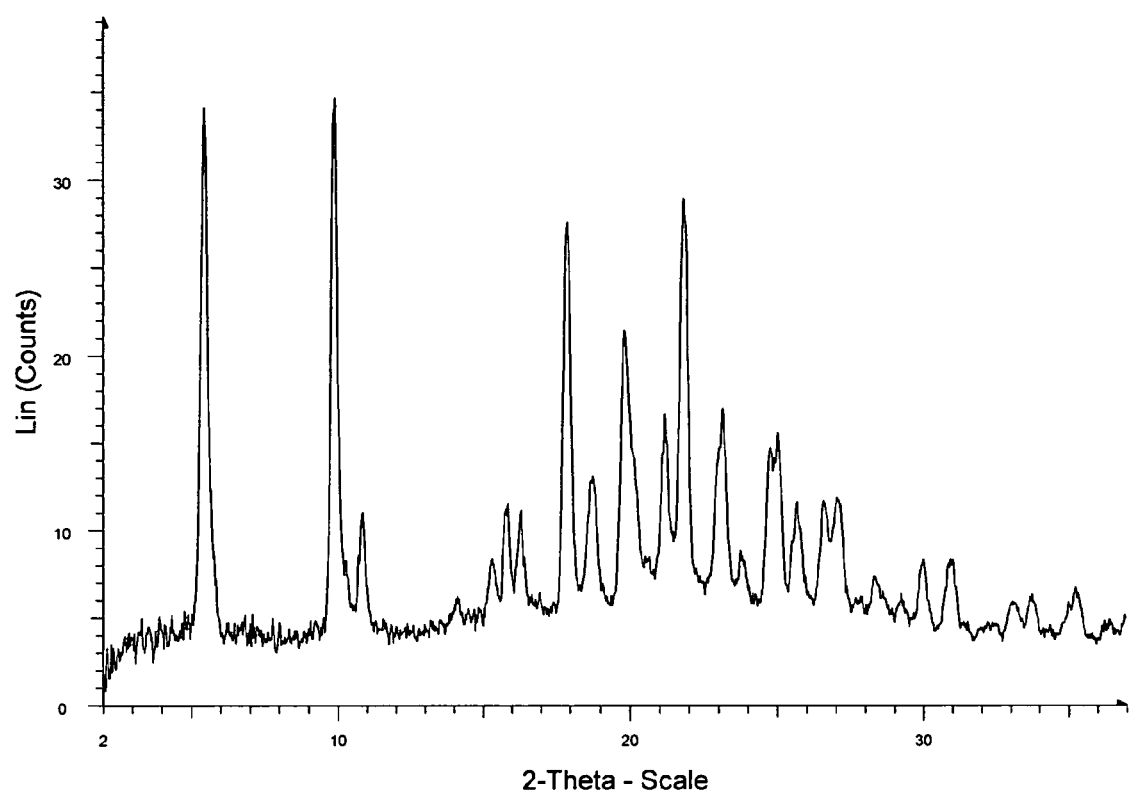
FIG. 10 shows a PXRD diffractogram of a 1:0.7:0.3 modafinil:succinic acid:fumaric acid mixed co-crystal.
Figure 11:
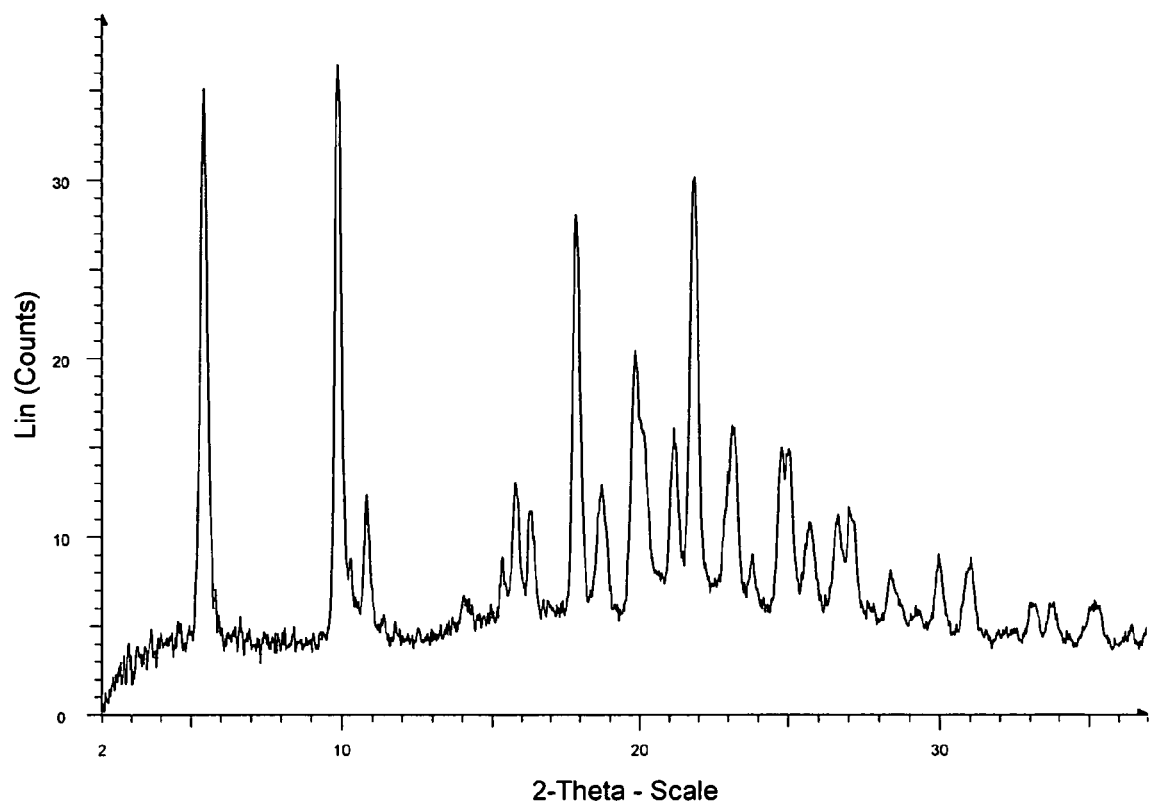
FIG. 11 shows a PXRD diffractogram of a 1:0.6:0.4 modafinil:succinic acid:fumaric acid mixed co-crystal.
Figure 12:
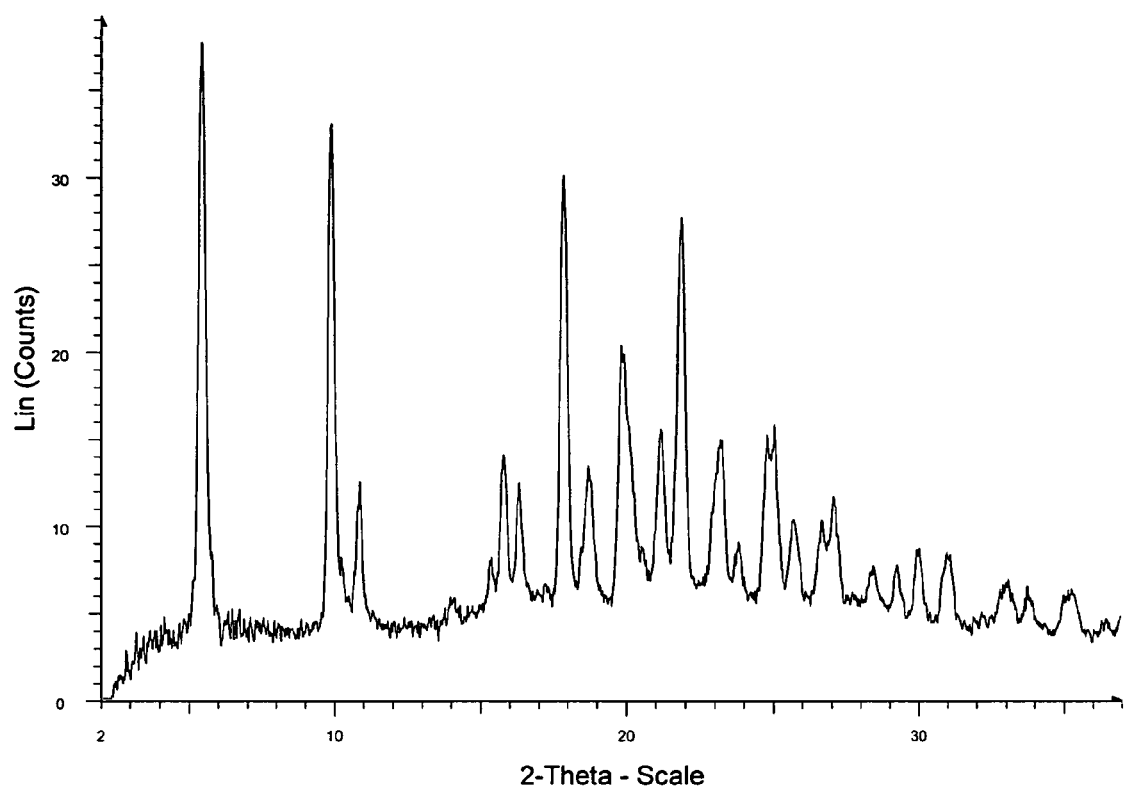
FIG. 12 shows a PXRD diffractogram of a 1:0.5:0.5 modafinil:succinic acid:fumaric acid mixed co-crystal.
Figure 13:
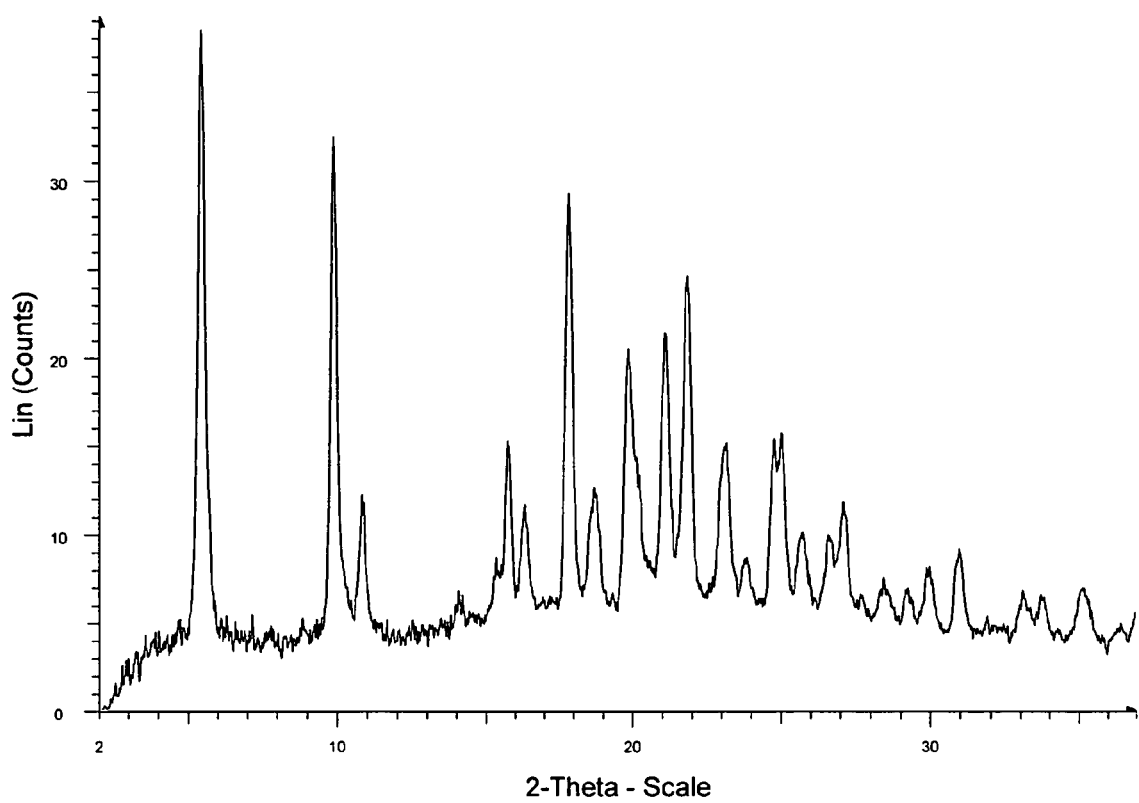
FIG. 13 shows a PXRD diffractogram of a 1:0.4:0.6 modafinil:succinic acid:fumaric acid mixed co-crystal.
Figure 14:
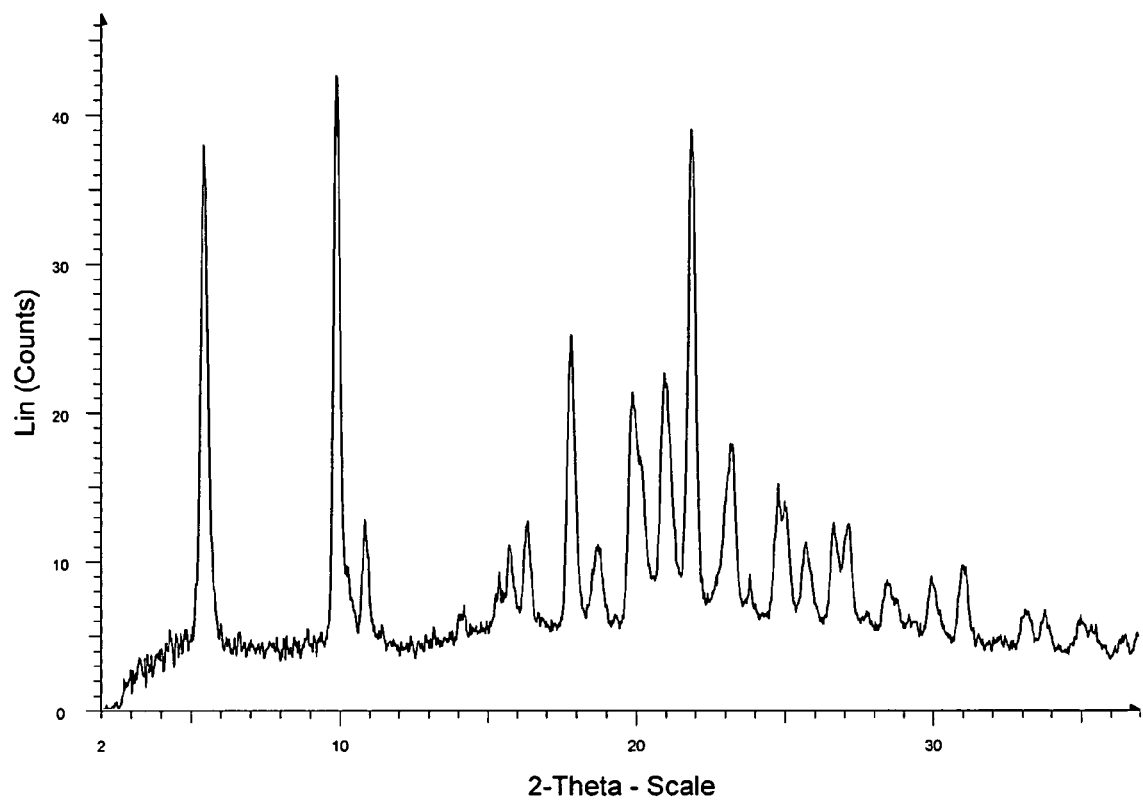
FIG. 14 shows a PXRD diffractogram of a 1:0.3:0.7 modafinil:succinic acid:fumaric acid mixed co-crystal.
Figure 15:
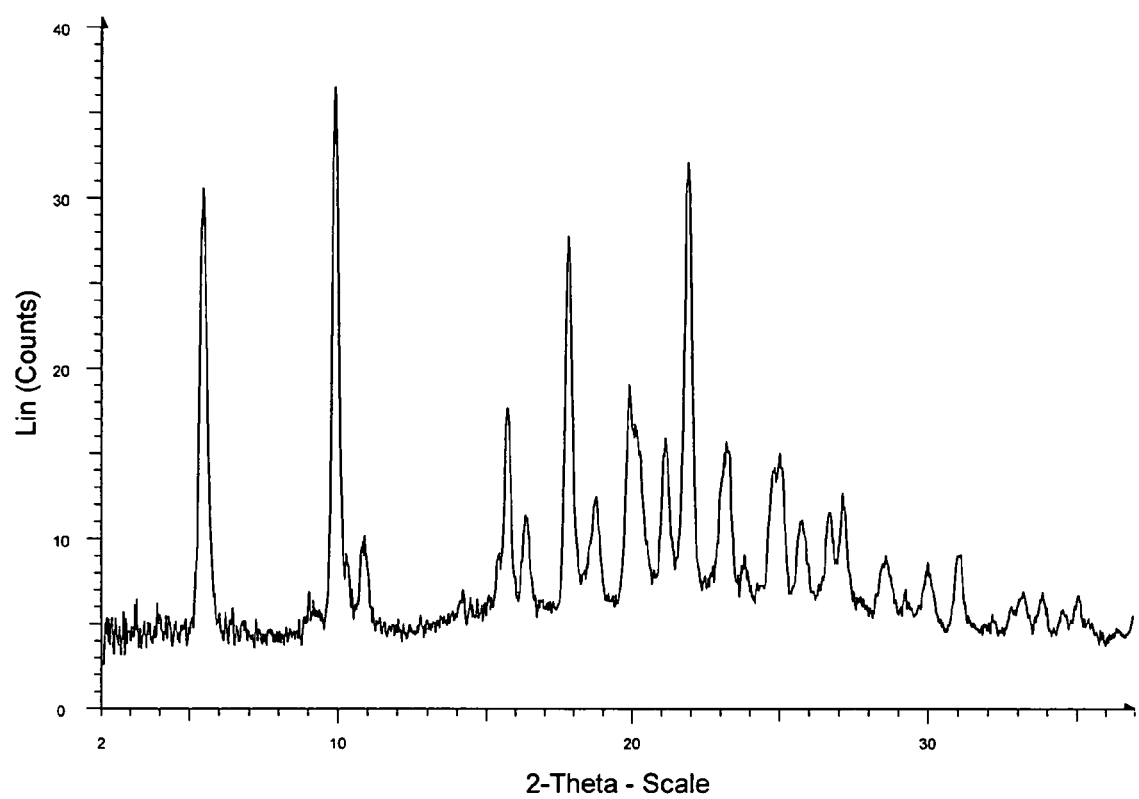
FIG. 15 shows a PXRD diffractogram of a 1:0.2:0.8 modafinil:succinic acid:fumaric acid mixed co-crystal.
Figure 16:
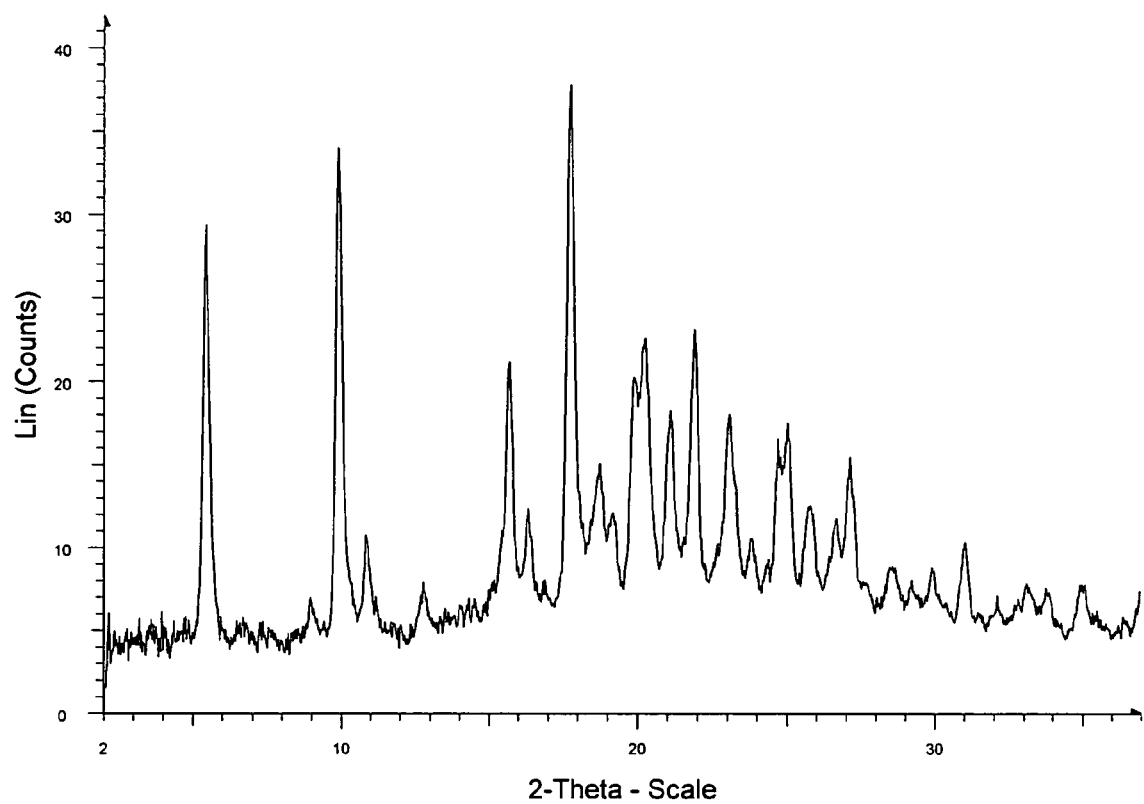
FIG. 16 shows a PXRD diffractogram of a 1:0.1:0.9 modafinil:succinic acid:fumaric acid mixed co-crystal.
Figure 17:
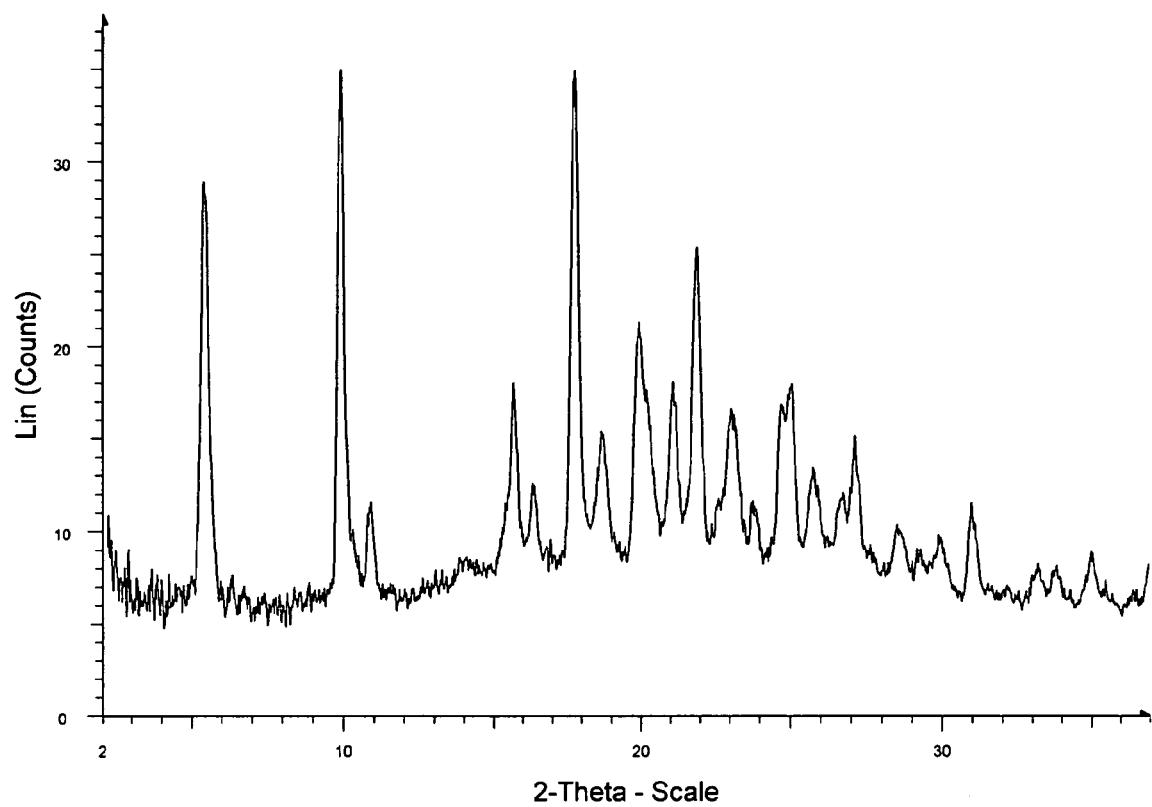
FIG. 17 shows a PXRD diffractogram of a 1:1 modafinil:fumaric acid co-crystal.

In another embodiment, the present invention provides modafinil:succinic acid:fumaric acid mixed co-crystals. In another embodiment, the present invention provides modafinil:succinic acid and modafinil:fumaric acid parent co-crystals. In another embodiment, a 1:0.1:0.9 modafinil:succinic acid:fumaric acid mixed co-crystal is provided. In another embodiment, a 1:0.2:0.8 modafinil:succinic acid:fumaric acid mixed co-crystal is provided. In another embodiment, a 1:0.3:0.7 modafinil:succinic acid:fumaric acid mixed co-crystal is provided. In another embodiment, a 1:0.4:0.6 modafinil:succinic acid:fumaric acid mixed co-crystal is provided. In another embodiment, a 1:0.5:0.5 modafinil:succinic acid:fumaric acid mixed co-crystal is provided. In another embodiment, a 1:0.6:0.4 modafinil:succinic acid:fumaric acid mixed co-crystal is provided. In another embodiment, a 1:0.7:0.3 modafinil:succinic acid:fumaric acid mixed co-crystal is provided. In another embodiment, a 1:0.8:0.2 modafinil:succinic acid:fumaric acid mixed co-crystal is provided. In another embodiment, a 1:0.9:0.1 modafinil:succinic acid:fumaric acid mixed co-crystal is provided. In another embodiment, a 1:0.1:0.9 modafinil:succinic acid:fumaric acid mixed co-crystal is provided, wherein its PXRD diffractogram is substantially the same as that shown in FIG. 16. In another embodiment, a 1:0.2:0.8 modafinil:succinic acid:fumaric acid mixed co-crystal is provided, wherein its PXRD diffractogram is substantially the same as that shown in FIG. 15. In another embodiment, a 1:0.3:0.7 modanifil:succinic acid:fumaric acid mixed co-crystal is provided, wherein its PXRD diffractogram is substantially the same as that shown in FIG. 14. In another embodiment, a 1:0.4:0.6 modafinil:succinic acid:fumaric acid mixed co-crystal is provided, wherein its PXRD diffractogram is substantially the same as that shown in FIG. 13. In another embodiment, a 1:0.5:0.5 modafinil:succinic acid:fumaric acid mixed co-crystal is provided, wherein its PXRD diffractogram is substantially the same as that shown in FIG. 12. In another embodiment, a 1:0.6:0.4 modafinil:succinic acid:fumaric acid mixed co-crystal is provided, wherein its PXRD diffractogram is substantially the same as that shown in FIG. 11. In another embodiment, a 1:0.7:0.3 modafinil:succinic acid:fumaric acid mixed co-crystal is provided, wherein its PXRD diffractogram is substantially the same as that shown in FIG. 10. In another embodiment, a 1:0.8:0.2 modafinil:succinic acid:fumaric acid mixed co-crystal is provided, wherein its PXRD diffractogram is substantially the same as that shown in FIG. 9. In another embodiment, a 1:0.9:0.1 modafinil:succinic acid:fumaric acid mixed co-crystal is provided, wherein its PXRD diffractogram is substantially the same as that shown in FIG. 8.

Solubility Modulation

In a further aspect, the present invention provides a process for modulating the solubility of an API, which process comprises:
(1) grinding, heating or contacting in solution the API with a co-crystal forming compound under crystallization conditions, so as to form a co-crystal of the API and the co-crystal forming compound; and
(2) isolating co-crystals comprising the API and the co-crystal forming compound.

In one embodiment, the solubility of the API is modulated such that the aqueous solubility is increased. Solubility of APIs may be measured by any conventional means such as chromatography (e.g., HPLC) or spectroscopic determination of the amount of API in a saturated solution of the API, such as UV-spectroscopy, IR-spectroscopy, Raman spectroscopy, quantitative mass spectroscopy, or gas chromatography.

In another aspect of the invention, the API may have low aqueous solubility. Typically, low aqueous solubility in the present application refers to a compound having a solubility in water which is less than or equal to 10 mg/mL, when measured at 37 degrees C., or less than or equal to 5 mg/mL or 1 mg/mL. Low aqueous solubility can further be specifically defined as less than or equal to 900, 800, 700, 600, 500, 400, 300, 200 150 100, 90, 80, 70, 60, 50, 40, 30, 20 micrograms/mL, or further 10, 5 or 1 micrograms/mL, or further 900, 800, 700, 600, 500, 400, 300, 200 150, 100 90, 80, 70, 60, 50, 40, 30, 20, or 10 ng/mL, or less than 10 ng/mL when measured at 37 degrees C. Aqueous solubility can also be specified as less than 500, 400, 300, 200, 150, 100, 75, 50 or 25 mg/mL. As embodiments of the present invention, solubility can be increased 2, 3, 4, 5, 7, 10, 15, 20, 25, 50, 75, 100, 200, 300, 500, 750, 1000, 5000, or 10,000 times by making a co-crystal of the reference form (e.g., crystalline or amorphous free acid, free base or zwitter ion, hydrate or solvate), or a salt thereof. Further aqueous solubility can be measured in simulated gastric fluid (SGF) or simulated intestinal fluid (SIF) rather than water. SGF (non-diluted) of the present invention is made by combining 1 g/L Triton X-100 and 2 g/L NaCl in water and adjusting the pH with 20 mM HCl to obtain a solution with a final pH=1.7 (SIF is 0.68% monobasic potassium phosphate, 1% pancreatin, and sodium hydroxide where the pH of the final solution is 7.5). The pH of the solvent used may also be specified as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 11.5, or 12, or any pH in between successive values.

Examples of embodiments includes: co-crystal compositions with an aqueous solubility, at 37 degrees C. and a pH of 7.0, that is increased at least 5 fold over the reference form, co-crystal compositions with a solubility in SGF that is increased at least 5 fold over the reference form, co-crystal compositions with a solubility in SIF that is increased at least 5 fold over the reference form.

Dissolution Modulation

In another aspect of the present invention, the dissolution profile of the API is modulated whereby the aqueous dissolution rate or the dissolution rate in simulated gastric fluid or in simulated intestinal fluid, or in a solvent or plurality of solvents is increased. Dissolution rate is the rate at which API solids dissolve in a dissolution medium. For APIs whose absorption rates are faster than the dissolution rates (e.g., steroids), the rate-limiting step in the absorption process is often the dissolution rate. Because of a limited residence time at the absorption site, APIs that are not dissolved before they are removed from intestinal absorption site are considered useless. Therefore, the rate of dissolution has a major impact on the performance of APIs that are poorly soluble. Because of this factor, the dissolution rate of APIs in solid dosage forms is an important, routine, quality control parameter used in the API manufacturing process.

Dissolution rate=K S($C_s$−C)

where K is dissolution rate constant, S is the surface area, $C_s$ is the apparent solubility, and C is the concentration of API in the dissolution medium.

For rapid API absorption, $C_s$−C is approximately equal to $C_s$

The dissolution rate of APIs may be measured by conventional means known in the art.

The increase in the dissolution rate of a co-crystal, as compared to the reference form (e.g., free form or salt), may be specified, such as by 10, 20, 30, 40, 50, 60, 70, 80, 90, or 100%, or by 2, 3, 4, 5 ,6, 7, 8, 9, 10, 15, 20, 25, 30, 40, 50, 75, 100, 125, 150, 175, 200, 250, 300, 350, 400, 500, 1000, 10,000, or 100,000 fold greater than the reference form (e.g., free form or salt form) in the same solution. Conditions under which the dissolution rate is measured is the same as discussed above. The increase in dissolution may be further specified by the time the composition remains supersaturated before reaching equilibrium solubility.

Examples of above embodiments include: co-crystal compositions with a dissolution rate in aqueous solution, at 37 degrees C. and a pH of 7.0, that is increased at least 5 fold over the reference form, co-crystal compositions with a dissolution rate in SGF that is increased at least 5 fold over the reference form, co-crystal compositions with a dissolution rate in SIF that is increased at least 5 fold over the reference form.

Bioavailability Modulation

The methods of the present invention are used to make a pharmaceutical API formulation with greater solubility, dissolution, and bioavailability. Bioavailability can be improved via an increase in AUC, reduced time to $T_{max}$, (the time to reach peak blood serum levels), or increased $C_{max}$. The present invention can result in higher plasma concentrations of API when compared to the neutral form or salt alone (reference form).

AUC is the area under the plot of plasma concentration of API (not logarithm of the concentration) against time after API administration. The area is conveniently determined by the "trapezoidal rule": The data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of APIs, and in estimating total clearance of APIs ($Cl_T$). Following single intravenous doses, AUC=D/$Cl_T$, for single compartment systems obeying first-order elimination kinetics, where D is the dose; alternatively, AUC=$C_0/k_{el}$, where $k_{el}$ is the API elimination rate constant. With routes other than the intravenous, for such systems, AUC=F·D/$Cl_T$, where F is the absolute bioavailability of the API.

Thus, in a further aspect, the present invention provides a process for modulating the bioavailability of an API when administered in its normal and effective dose range as a co-crystal, whereby the AUC is increased, the time to $T_{max}$ is reduced, or $C_{max}$ is increased, as compared to a reference form, which process comprises:

(1) grinding, heating or contacting in solution the API with a co-crystal forming compound under crystallization conditions, so as to form a co-crystal of the API and the co-crystal forming compound; and (2) isolating co-crystals comprising the API and the co-crystal forming compound.

Examples of the above embodiments include: co-crystal compositions with a time to $T_{max}$ that is reduced by at least 10% as compared to the reference form, co-crystal compositions with a time to $T_{max}$ that is reduced by at least 20% over the reference form, co-crystal compositions with a time to $T_{max}$ that is reduced by at least 40% over the reference form, co-crystal compositions with a time to $T_{max}$ that is reduced by at least 50% over the reference form, co-crystal compositions with a $T_{max}$ that is reduced by at least 60% over the reference form, co-crystal compositions with a $T_{max}$ that is reduced by at least 70% over the reference form, co-crystal compositions with a $T_{max}$ that is reduced by at least 80% over the reference form, co-crystal compositions with a $T_{max}$ that is reduced by at least 90% over the reference form, co-crystal compositions with a $C_{max}$ that is increased by at least 20% over the reference form, co-crystal compositions with a $C_{max}$ that is increased by at least 30% over the reference form, co-crystal compositions with a $C_{max}$ that is increased by at least 40% over the reference form, co-crystal compositions with a $C_{max}$ that is increased by at least 50% over the reference form, co-crystal compositions with a $C_{max}$ that is increased by at least 60% over the reference form, co-crystal compositions with a $C_{max}$ that is increased by at least 70% over the reference form, co-crystal compositions with a $C_{max}$ that is increased by at least 80% over the reference form, co-crystal compositions with a $C_{max}$ that is increased by at least 2 fold, 3 fold, 5 fold, 7.5 fold, 10 fold, 25 fold, 50 fold or 100 fold, co-crystal compositions with an AUC that is increased by at least 10% over the reference form, co-crystal compositions with an AUC that is increased by at least 20% over the reference form, co-crystal compositions with an AUC that is increased by at least 30% over the reference form, co-crystal compositions with an AUC that is increased by at least 40% over the reference form, co-crystal compositions with an AUC that is increased by at least 50% over the reference form, co-crystal compositions with an AUC that is increased by at least 60% over the reference form, co-crystal compositions with an AUC that is increased by at least 70% over the reference form, co-crystal compositions with an AUC that is increased by at least 80% over the reference form or co-crystal compositions with an AUC that is increased by at least 2 fold, 3 fold, 4 fold, 5 fold, 6 fold, 7 fold, 8 fold, 9 fold, or 10 fold. Other examples include wherein the reference form is crystalline, wherein the reference form is amorphous, wherein the reference form is an anhydrous crystalline sodium salt, or wherein the reference form is an anhydrous crystalline HCl salt.

Dose Response Modulation

In a further aspect the present invention provides a process for improving the dose response of an API, which process comprises:
(1) contacting in solution an API with a co-crystal forming compound under crystallization conditions, so as to form a co-crystal of the API and the co-crystal forming compound; and
(2) isolating co-crystals comprising the API and the co-crystal forming compound.

Dose response is the quantitative relationship between the magnitude of response and the dose inducing the response and may be measured by conventional means known in the art. The curve relating effect (as the dependent variable) to dose (as the independent variable) for an API-cell system is the "dose-response curve". Typically, the dose-response curve is the measured response to an API plotted against the dose of the API (mg/kg) given. The dose response curve can also be a curve of AUC against the dose of the API given.

In an embodiment of the present invention, a co-crystal of the present invention has an increased dose response curve or a more linear dose response curve than the corresponding reference compound.

Increased Stability

In a still further aspect the present invention provides a process for improving the stability of an API (as compared to a reference form such as its free form or a salt thereof), which process comprises:
(1) grinding, heating or contacting in solution the pharmaceutical salt with a co-crystal forming compound under crystallization conditions, so as to form a co-crystal of the API and the co-crystal forming compound; and
(2) isolating co-crystals comprising the API and the co-crystal forming compound.

In another embodiment, the compositions of the present invention, including the API or active pharmaceutical ingredient (API) and formulations comprising the API, are suitably stable for pharmaceutical use. In another embodiment, the API or formulations thereof of the present invention are stable such that when stored at 30 degrees C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. In another embodiment, when stored at 40 degrees C. for 2 years, less than 0.2% of any one degradant is formed. Alternatively, when stored at 30 degrees C. for 3 months, less than 0.2% or 0.15%, or 0.1% of any one degradant is formed, or when stored at 40 degrees C. for 3 months, less than 0.2% or 0.15%, or 0.1% of any one degradant is formed. Further alternatively, when stored at 60 degrees C. for 4 weeks, less than 0.2% or 0.15%, or 0.1% of any one degradant is formed. The relative humidity (RH) may be specified as ambient (RH), 75% (RH), or as any single integer between 1 to 99%.

Difficult to Salt or Unsaltable Compounds

In a still further aspect the present invention provides a process for making co-crystals of unsaltable or difficult to salt APIs which process comprises:
(1) grinding, heating or contacting in solution an API with a co-crystal forming compound under crystallization conditions, so as to form a co-crystal of the API and the co-crystal forming compound; and
(2) isolating co-crystals comprising the API and the co-crystal forming compound.

Difficult to salt compounds include bases with a pKa<3 or acids with a pKa>10. Zwitter ions are also difficult to salt or unsaltable compounds according to the present invention.

Decreasing Hygroscopicity

In a still further aspect, the present invention provides a method for decreasing the hygroscopicity of an API, which method comprises:
(1) grinding, heating or contacting in solution the API with a co-crystal forming compound under crystallization conditions, so as to form a co-crystal of the API and the co-crystal forming compound; and
(2) isolating co-crystals comprising the API and the co-crystal forming compound.

An aspect of the present invention provides a pharmaceutical composition comprising a co-crystal of an API that is less hygroscopic than amorphous or crystalline, free form or salt (including metal salts such as sodium, potassium, lithium, calcium, magnesium) or another reference compound. Hygroscopicity can be assessed by dynamic vapor sorption analysis, in which 5-50 mg of the compound is suspended from a Cahn microbalance. The compound being analyzed should be placed in a non-hygroscopic pan and its weight should be measured relative to an empty pan composed of identical material and having nearly identical size, shape, and weight. Ideally, platinum pans should be used. The pans should be suspended in a chamber through which a gas, such as air or nitrogen, having a controlled and known percent relative humidity (% RH) is flowed until eqilibrium criteria are met. Typical equilibrium criteria include weight changes of less than 0.01% over 3 minutes at constant humidity and temperature. The relative humidity should be measured for samples dried under dry nitrogen to constant weight (<0.01% change in 3 minutes) at 40 degrees C. unless doing so would de-solvate or otherwise convert the material to an amorphous compound. In one aspect, the hygroscopicity of a dried compound can be assessed by increasing the RH from 5 to 95% in increments of 5% RH and then decreasing the RH from 95 to 5% in 5% increments to generate a moisture sorption isotherm. The sample weight should be allowed to equilibrate between each change in % RH. If the compound deliquesces or becomes amorphous above 75% RH, but below 95% RH, the experiment should be repeated with a fresh sample and the relative humidity range for the cycling should be narrowed to 5-75% RH or 10-75% RH, instead of 5-95% RH. If the sample cannot be dried prior to testing due to lack of form stability, than the sample should be studied using two complete humidity cycles of either 10-75% RH or 5-95% RH, and the results of the second cycle should be used if there is significant weight loss at the end of the first cycle.

Hygroscopicity can be defined using various parameters. For purposes of the present invention, a non-hygroscopic molecule should not gain or lose more than 1.0%, or 0.5% weight at 25 degrees C. when cycled between 10 and 75% RH (relative humidity at 25 degrees C.). The non-hygroscopic molecule, for example, should not gain or lose more than 1.0%, or 0.5% weight when cycled between 5 and 95% RH at 25 degrees C., or more than 0.25% of its weight between 10 and 75% RH. In another embodiment, a non-hygroscopic molecule will not gain or lose more than 0.25% of its weight when cycled between 5 and 95% RH.

Alternatively, for purposes of the present invention, hygroscopicity can be defined using the parameters of Callaghan et al., "Equilibrium moisture content of pharmaceutical excipients", in Api Dev. Ind. Pharm., Vol. 8, pp. 335-369 (1982). Callaghan et al. classified the degree of hygroscopicity into four classes.

| | |
|---|---|
| Class 1: Non-hygroscopic | Essentially no moisture increases occur at relative humidities below 90%. |
| Class 2: Slightly hygroscopic | Essentially no moisture increases occur at relative humidities below 80%. |
| Class 3: Moderately hygroscopic | Moisture content does not increase more than 5% after storage for 1 week at relative humidities below 60%. |
| Class 4: Very hygroscopic | Moisture content increase may occur at relative humidities as low as 40 to 50%. |

Alternatively, for purposes of the present invention, hygroscopicity can be defined using the parameters of the European Pharmacopoeia Technical Guide (1999, p. 86) which has defined hygrospocity, based on the static method, after storage at 25 degrees C. for 24hours at 80% RH:

Slightly hygroscopic: Increase in mass is less than 2 percent m/m and equal to or greater than 0.2 percent m/m.

Hygroscopic: Increase in mass is less than 15 percent m/m and equal to or greater than 0.2 percent m/m.

Very Hygroscopic: Increase in mass is equal to or greater than 15 percent m/m.

Deliquescent: Sufficient water is absorbed to form a liquid.

Co-crystals of the present invention can be set forth as being in Class 1, Class 2, or Class 3, or as being Slightly hygroscopic, Hygroscopic, or Very Hygroscopic. Co-crystals of the present invention can also be set forth based on their ability to reduce hygroscopicity. Thus, co-crystals of the present invention can be less hygroscopic than a reference compound. The reference compound can be specified as the API in free form (free acid, free base, hydrate, solvate, etc.) or salt (e.g., especially metal salts such as sodium, potassium, lithium, calcium, or magnesium). Further included in the present invention are co-crystals that do not gain or lose more than 1.0% weight at 25 degrees C. when cycled between 10 and 75% RH, wherein the reference compound gains or loses more than 1.0% weight under the same conditions. Further included in the present invention are co-crystals that do not gain or lose more than 0.5% weight at 25 degrees C. when cycled between 10 and 75% RH, wherein the reference compound gains or loses more than 0.5% or more than 1.0% weight under the same conditions. Further included in the present invention are co-crystals that do not gain or lose more than 1.0% weight at 25 degrees C. when cycled between 5 and 95% RH, wherein the reference compound gains or loses more than 1.0% weight under the same conditions. Further included in the present invention are co-crystals that do not gain or lose more than 0.5% weight at 25 degrees C. when cycled between 5 and 95% RH, wherein the reference compound gains or loses more than 0.5% or more than 1.0% weight under the same conditions. Further included in the present invention are co-crystals that do not gain or lose more than 0.25% weight at 25 degrees C. when cycled between 5 and 95% RH, wherein the reference compound gains or loses more than 0.5% or more than 1.0% weight under the same conditions.

Further included in the present invention are co-crystals that have a hygroscopicity (according to Callaghan et al.) that is at least one class lower than the reference compound or at least two classes lower than the reference compound. Included are a Class 1 co-crystal of a Class 2 reference compound, a Class 2 co-crystal of a Class 3 reference compound, a Class 3 co-crystal of a Class 4 reference compound, a Class 1 co-crystal of a Class 3 reference compound, a Class 1 co-crystal of a Class 4 reference compound, or a Class 2 co-crystal of a Class 4 reference compound.

Further included in the present invention are co-crystals that have a hygroscopicity (according to the European Pharmacopoeia Technical Guide) that is at least one class lower than the reference compound or at least two classes lower than the reference compound. Non-limiting examples include; a slightly hygroscopic co-crystal of a hygroscopic reference compound, a hygroscopic co-crystal of a very hygroscopic reference compound, a very hygroscopic co-crystal of a deliquescent reference compound, a slightly hygroscopic co-crystal of a very hygroscopic reference compound, a slightly hygroscopic co-crystal of a deliquescent reference compound, and a hygroscopic co-crystal of a deliquescent reference compound.

Crystallizing Amorphous Compounds

In a further aspect, the present invention provides a process for crystallizing an amorphous compound, which process comprises:

(1) grinding, heating or contacting in solution the API with a co-crystal forming compound under crystallization conditions, so as to form a co-crystal of the API and the co-crystal forming compound; and (2) isolating co-crystals comprising the API and the co-crystal forming compound.

An amorphous compound includes compounds that do not crystallize using routine methods in the art.

Decreasing Form Diversity

In a still further embodiment aspect the present invention provides a process for reducing the form diversity of an API, which process comprises:

(1) grinding, heating or contacting in solution the API with a co-crystal forming compound under crystallization conditions, so as to form a co-crystal of the API and the co-crystal forming compound; and (2) isolating co-crystals comprising the API and the co-crystal forming compound.

For purposes of the present invention, the number of forms of a co-crystal is compared to the number of forms of a reference compound (e.g. the free form or a salt of the API) that can be made using routine methods in the art.

Morphology Modulation

In a still further aspect the present invention provides a process for modifying the morphology of an API, which process comprises:
(1) grinding, heating or contacting in solution the API with a co-crystal forming compound under crystallization conditions, so as to form a co-crystal of the API and the co-crystal forming compound; and
(2) isolating co-crystals comprising the API and the co-crystal forming compound.

In an embodiment the co-crystal comprises or consists of a co-crystal former and a pharmaceutical wherein the interaction between the two, e.g., H-bonding, occurs between a functional group of an API with a corresponding interacting group of a co-crystal former. In a further embodiment, the co-crystal comprises a co-crystal former and an API with a corresponding interacting group. In an aspect of the invention, only co-crystals having an H-bond acceptor on the first molecule and an H-bond donor on the second molecule, where the first and second molecules are either co-crystal former and API respectively or API and co-crystal former respectively, are included in the present invention.

In another embodiment, the co-crystal former and API each have only one H-bond donor/acceptor. In another aspect, the molecular weight of the API is less than 2000, 1500, 1000, 750, 500, 350, 200, or 150 Daltons. In another embodiment, the molecular weight of the API is between 100-200, 200-300, 300-400, 400-500, 500-600, 600-700, 700-800, 800-900, 900-1000, 1000-1200, 1200-1400, 1400-1600, 1600-1800, or 1800-2000 amu. APIs with the above molecular weights may also be specifically excluded from the present invention.

In another embodiment, peptides, proteins, nucleic acids or other biological APIs are excluded from the present invention. In another embodiment, all non-pharmaceutically acceptable co-crystal formers are excluded from the present invention. In another embodiment, organometallic APIs are excluded from the present invention. Any APIs currently known in the art may also be specifically excluded from the present invention. For example, carbamazepine, itraconazole, nabumetone, fluoxetine, acetaminophen and theophylline can each be specifically excluded from the present invention. In another embodiment, the API is not a salt, is not a non-metal salt, or is not a metal salt, e.g., sodium, potassium, lithium, calcium or magnesium. In another embodiment, the API is a salt, is a non-metal salt, or is a metal salt, e.g., sodium, potassium, lithium, calcium, magnesium. In one embodiment, the API does not contain a halogen. In one embodiment, the API does contain a halogen.

In another embodiment, any one or more APIs may be specifically excluded from the present invention. Any APIs currently known in the art may also be specifically excluded from the present invention.

Excipients employed in pharmaceutical compositions of the present invention can be solids, semi-solids, liquids or combinations thereof. Compositions of the invention containing excipients can be prepared by any known technique of pharmacy that comprises admixing an excipient with an API or therapeutic agent. A pharmaceutical composition of the invention contains a desired amount of API per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the API, such as tablets or capsules.

In another embodiment, APIs with an inappropriate pH for transdermal patches can be co-crystallized with an appropriate co-crystal former, thereby adjusting its pH to an appropriate level for use as a transdermal patch. In another embodiment, an APIs pH level can be optimized for use in a transdermal patch via co-crystallization with an appropriate co-crystal former.

Non-limiting examples follow of excipients that can be used to prepare pharmaceutical compositions of the invention.

Pharmaceutical compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, about 10% to about 85%, or about 20% to about 80%, of the total weight of the composition. The carrier, carriers, diluent, or diluents selected, optionally, exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are optional diluents. These diluents are chemically compatible with many co-crystals described herein. The use of extragranular microcrystalline cellulose (that is, microcrystalline cellulose added to a granulated composition) can be used to improve hardness (for tablets) and/or disintegration time. Lactose, especially lactose monohydrate, can be used. Lactose typically provides compositions having suitable release rates of co-crystals, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colorcon™

1500), clays (e.g., Veegum™ HV of R. T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, about 0.2% to about 10%, or about 0.2% to about 5%, of the total weight of the composition.

Croscarmellose sodium can be used as a disintegrant for tablet or capsule disintegration, and, if present, can constitute about 0.2% to about 10%, about 0.2% to about 7%, or about 0.2% to about 5%, of the total weight of the composition. Croscarmellose sodium confers superior intragranular disintegration capabilities to granulated pharmaceutical compositions of the present invention.

Pharmaceutical compositions of the invention optionally comprise one or more pharmaceutically acceptable binding agents or adhesives as excipients, particularly for tablet formulations. Such binding agents and adhesives can impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a co-crystal of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, about 0.75% to about 15%, or about 1% to about 10%, of the total weight of the pharmaceutical composition.

Many of the binding agents are polymers comprising amide, ester, ether, alcohol or ketone groups and, as such, can be included in pharmaceutical compositions of the present invention. For example, polyvinylpyrrolidones such as povidone K-30. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Such wetting agents are optionally selected to maintain the co-crystal in close association with water, a condition that is believed to improve bioavailability of the composition. Such wetting agents can also be useful in solubilizing or increasing the solubility of co-crystals.

Non-limiting examples of surfactants that can be used as wetting agents in pharmaceutical compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees Ctoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the pharmaceutical composition.

Wetting agents that are anionic surfactants can be used. For example, sodium lauryl sulfate. Sodium lauryl sulfate, if present, constitutes about 0.25% to about 7%, about 0.4% to about 4%, or about 0.5% to about 2%, of the total weight of the pharmaceutical composition.

Pharmaceutical compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the pharmaceutical composition.

Magnesium stearate is a lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is an anti-adherent or glidant used, for example, to reduce formulation sticking to equipment surfaces and also to reduce static in the blend. Talc, if present, constitutes about 0.1% to about 10%, about 0.25% to about 5%, or about 0.5% to about 2%, of the total weight of the pharmaceutical composition.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is a suitable glidant.

Other excipients such as colorants, flavors and sweeteners are known in the pharmaceutical art and can be used in pharmaceutical compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions of the invention. When present in pharmaceutical compositions of the invention to promote dosage form disintegration, one or more effervescent agents are optionally present in a total amount of about 30% to about 75%, about 45% to about 70%, or about 60%, by weight of the pharmaceutical composition.

According to another embodiment of the invention, an effervescent agent, present in a solid dosage form in an amount less than that effective to promote disintegration of the dosage form, provides improved dispersion of the API in an aqueous medium. Without being bound by theory, it is believed that the effervescent agent is effective to accelerate dispersion of the API from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is optionally present in an amount of about 1% to about 20%, about 2.5% to about 15%, or about 5% to about 10%, by weight of the pharmaceutical composition.

An "effervescent agent" herein is an agent comprising one or more compounds which, acting together or individually, evolve a gas on contact with water. The gas evolved is generally oxygen or, most commonly, carbon dioxide. Effervescent agents can comprise an acid and a base that react in the presence of water to generate carbon dioxide gas. Optionally, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof.

Non-limiting examples of suitable acids as components of effervescent agents and/or solid organic acids useful in the invention include citric acid, tartaric acid (as D-, L-, or D/L-tartaric acid), malic acid (as D-, L-, or DL-malic acid), maleic acid, fumaric acid, adipic acid, succinic acid, acid anhydrides of such acids, acid salts of such acids, and mixtures thereof.

In another embodiment of the invention, where the effervescent agent comprises an acid and a base, the weight ratio of the acid to the base is about 1:100 to about 100:1, about 1:50 to about 50:1, or about 1:10 to about 10:1. In a further embodiment of the invention, where the effervescent agent comprises an acid and a base, the ratio of the acid to the base is approximately stoichiometric.

Excipients which solubilize APIs typically have both hydrophilic and hydrophobic regions, or can be amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a poly-alkylene glycol to produce a mixture of mono-, di- and triglycerides and mono- and di-esters; e.g., stearoyl macrogol-32 glycerides). Such pharmaceutical compositions are advantageously administered orally.

Pharmaceutical compositions of the present invention can comprise about 10% to about 50%, about 25% to about 50%, about 30% to about 45%, or about 30% to about 35% by weight of a co-crystal; about 10% to about 50%, about 25% to about 50%, about 30% to about 45%, or about 30% to about 35% by weight of an excipient which inhibits crystallization in aqueous solution, in simulated gastric fluid, or in simulated intestinal fluid; and about 5% to about 50%, about 10% to about 40%, about 15% to about 35%, or about 30% to about 35% by weight of a binding agent. In one example, the weight ratio of the co-crystal to the excipient which inhibits crystallization to binding agent is about 1 to 1 to 1.

Solid dosage forms of the invention can be prepared by any suitable process, not limited to processes described herein.

An illustrative process comprises (a) a step of blending an API of the invention with one or more excipients to form a blend, and (b) a step of tableting or encapsulating the blend to form tablets or capsules, respectively.

In another process, solid dosage forms are prepared by a process comprising (a) a step of blending a co-crystal of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is optionally a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are optionally added, for example in the blending step, a wetting agent can optionally be added, for example in the granulating step, and one or more disintegrants are optionally added after granulating but before tableting or encapsulating. A lubricant is optionally added before tableting. Blending and granulating can be performed independently under low or high shear. A process is optionally selected that forms a granulate that is uniform in API content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein an API is suspended with one or more excipients in one or more sprayable liquids, optionally a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention can be selected to provide a disintegration time of less than about 30 minutes, about 25 minutes or less, about 20 minutes or less, or about 15 minutes or less, in a standard disintegration assay.

Forms of modafinil as well as many other APIs can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 Technomic Publishing, Lancaster, Pa.: 2000). In the present invention, greater targeting of the liver and the sites of lipid particle generation could be an advantage of controlled release.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions.

One embodiment of the invention encompasses a unit dosage form which comprises an API, and one or more pharmaceutically acceptable excipients or diluents, wherein the pharmaceutical composition or dosage form is formulated for controlled-release. Specific dosage forms utilize an osmotic drug delivery system.

An example of a delayed-release dosage form that also functions as a time controlled-release dosage form is described in U.S. Pat. No. 5,366,738, herein incorporated by reference in its entirety. The controlled-release drug delivery device described in U.S. Pat. No. 5,366,738 is known as a gel extrusion module (GEM) delivery device. The GEM device is a drug delivery device for the controlled in situ production and release of a dispersion containing a beneficial agent such as a pharmaceutical drug comprising:

(A) a compressed core prepared from an admixture comprising:
  (i) a therapeutically effective amount of the beneficial agent; and
  (ii) a polymer which upon hydration forms gelatinous microscopic particles; and
(B) a water insoluble, water impermeable polymeric coating comprising a polymer and a plasticizer, which surrounds and adheres to the core, the coating having a plurality of formed apertures exposing between about 1 and about 75% of the core surface;

and wherein the release rate of the beneficial agent from the device is a function of the number and size of the apertures.

In the GEM device, the polymer inside the compressed core is selected from materials such as sodium polyacrylate, carboxypolymethylenes and the pharmaceutically acceptable salts thereof such as a sodium salt, wherein the carboxypolymethylenes are prepared from acrylic acid crosslinked with allylethers of sucrose or pentaerythritol, and, for example, it is selected from carboxypolymethylenes prepared from acrylic acid crosslinked with allylethers of sucrose or pentaerythritol, and the pharmaceutically acceptable salts thereof. Often CARBOPOL® 974P and pharmaceutically acceptable salts thereof, particularly the sodium salt, is used as the polymer inside the compressed core. In addition, the compressed core may also contain one or more polymer hydration modulating agents, anti-oxidants, lubricants, fillers and excipients. An optional subcoating may be applied to the compressed core prior to application of the water insoluble coating as an aid in the manufacturing process. The subcoating may be comprised of, for example, hydroxypropyl cellulose and hydroxypropylmethylcellulose. Additional coatings may be applied for aesthetic or functional purposes.

The water insoluble, water impermeable polymeric coating is comprised of, for example, (1) a polymer selected from polyvinyl chloride, cellulose acetate, cellulose acetate butyrate, ethylcellulose and combinations of these polymers; and (2) a plasticizer selected from diethylphthalate, dibutylsebacate and triethylcitrate. For example, the polymeric coating is comprised of cellulose acetate butyrate and triethyl citrate. The GEM device does not function as an osmotic drug delivery device, hence the release function of the device depends on passage of fluids from the external environment of the body to the internal environment of the compressed core through the formed apertures. It is intended that the terms "water insoluble, water impermeable" used to describe the polymeric coating define a coating which is essentially water insoluble and water impermeable, meaning that the polymeric coating allows minimal to no passage of water through the coating from the external environment of the body to the internal environment of the compressed core, except for the fluid passage that occurs through the drilled apertures, during the period of time the drug is being released from the GEM device in the body. Any minimal amount of water that does pass through the water insoluble, water impermeable polymeric coating is insubstantial and does not significantly contribute to the function of the GEM device, i.e.

the release rate of the drug through the apertures. Rather the release rate of the API from the GEM device is primarily a function of the number and size of the apertures on the device.

For an elegant, aesthetically pleasing final product, an outer finish coat may finally be applied to the GEM delivery device containing colorants, waxes, and the like. The GEM device can also be enterically coated, either before or after the application of additional finish coatings. Even without enteric coating, extrusion of the polymer which carries the API out from inside the compressed core of the GEM device does not occur to a substantial extent in the acidic pH of the stomach, therefore substantial release of the API should not occur in the stomach. Further details and examples of the GEM delivery device are described in U.S. Pat. No. 5,366,738.

The invention further provides a medicament or a pharmaceutical composition comprising a mixed co-crystal of modafinil and methods of making the same. Typically, the medicament or pharmaceutical composition further comprises one or more pharmaceutically-acceptable carriers, diluents or excipients.

The processes according to the present invention may each comprise a further step or steps in which the modafinil co-crystal produced thereby is incorporated into a medicament or a pharmaceutical composition.

In a still further aspect of the invention, a method is provided for treating a subject, for example a human subject, suffering from excessive daytime sleepiness associated with narcolepsy, multiple sclerosis related fatigue, infertility, eating disorders, attention deficit hyperactivity disorder (ADHD), Parkinson's disease, incontinence, sleep apnea, or myopathies where modafinil is an effective active pharmaceutical for said disorder. The method comprises administering to the subject a therapeutically-effective amount of a mixed co-crystal comprising modafinil.

In a still further aspect of the invention, a method is provided for the treatment of neoplasia including cancer, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-Lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). The method comprises administering to the subject a therapeutically-effective amount of a mixed co-crystal or a co-crystal comprising urea.

The invention will now be described in further detail, by way of example, with reference to the accompanying drawings.

EXEMPLIFICATION

General Methods for the Preparation of Co-Crystals a) High Throughput Crystallization using the CrystalMax Platform CrystalMax™ comprises a sequence of automated, integrated high throughput robotic stations capable of rapid generation, identification and characterization of polymorphs, salts, and co-crystals of APIs and API candidates. Worksheet generation and combinatorial mixture design is carried out using proprietary design software InForm™. Typically, an API or an API candidate is dispensed from an organic solvent into tubes and dried under a stream of nitrogen. Salts and/or co-crystal formers may also be dispensed and dried in the same fashion. Water and organic solvents may be combinatorially dispensed into the tubes using a multi-channel dispenser. Each tube in a 96-tube array is then sealed within 15 seconds of combinatorial dispensing to avoid solvent evaporation. The mixtures are then rendered supersaturated by heating to 70 degrees C. for 2 hours followed by a 1 degree C./minute cooling ramp to 5 degrees C. Optical checks are then conducted to detect crystals and/or solid material. Once a solid has been identified in a tube, it is isolated through aspiration and drying. Raman spectra are then obtained on the solids and cluster classification of the spectral patterns is performed using proprietary software (QForm™).

b) Crystallization from Solution

Co-crystals may be obtained by dissolving the separate components in a solvent and adding one to the other. The co-crystal may then precipitate or crystallize as the solvent mixture is evaporated slowly. The co-crystal may also be obtained by dissolving the components in the same solvent or a mixture of solvents.

c) Crystallization from the Melt

A co-crystal may be obtained by melting the co-crystal components together and allowing recrystallization to occur. In some cases, an anti-solvent may be added to facilitate crystallization.

d) Thermal Microscopy

A co-crystal may be obtained by melting the higher melting component on a glass slide and allowing it to recrystallize. The second component is then melted and is also allowed to recrystallize. The co-crystal may form as a separated phase /band in between the eutectic bands of the original components.

e) Mixing and/or Grinding

A co-crystal may be obtained by mixing or grinding two or more components together in the solid state.

Analytical Methods

Procedure for DSC Analysis

DSC analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 ($^8$2001 TA Instruments-Water LLC). In addition, the analysis software used was Universal Analysis 2000 for Windows 95/95/2000/NT, version 3.1 E;Build 3.1.0.40 ($^8$2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing $\leq 2$ mg of sample in an aluminum pan with a crimped pan closure. The starting temperature was typically 20 degrees C. with a heating rate of 10 degrees C./minute, and the ending temperature was 300 degrees C. Unless otherwise indicated, all reported transitions are as stated +/−1.0 degrees C.

Procedure for PXRD Analysis

A powder X-ray diffraction (PXRD) pattern for the samples was obtained using a D/Max Rapid, Contact (Rigaku/MSC, The Woodlands, Tex., U.S.A.), which uses as its control software RINT Rapid Control Software, Rigaku Rapid/XRD, version 1.0.0 (1999 Rigaku Co.). In addition, the analysis software used were RINT Rapid display software, version 1.18 (Rigaku/MSC), and JADE XRD Pattern Processing, versions 5.0 and 6.0 ((1995-2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-60 degrees; the integration chi range was 0-360 degrees; the number of chi segments was 1; the step size used was 0.02; the integration utility was cylint; normalization was used; dark counts were 8; omega offset was 180; and chi and phi offsets were 0.

PXRD diffractograms were also acquired via the Bruker AXS D8 Discover X-ray Diffractometer. This instrument was equipped with GADDS™ (General Area Diffraction Detection System), a Bruker AXS HI-STAR Area Detector at a distance of 15.05 cm as per system calibration, a copper source ($Cu/K_\alpha$ 1.54056 angstroms), automated x-y-z stage, and 0.5 mm collimator. The sample was compacted into pellet form and mounted on the x-y-z stage. A diffractogram was acquired under ambient conditions (25 degrees C.) at a powder setting of 40 kV and 40 mA in reflection mode while the sample remained stationary. The exposure time was varied and specified for each sample. The diffractogram obtained underwent a spatial remapping procedure to account for the geometrical pincushion distortion of the area detector then integrated along chi from −118.8 to −61.8 degrees and 2-theta 2.1-37 degrees at a step size of 0.02 degrees with normalization set to bin normalize.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.1 degrees 2-theta.

For PXRD data herein, including Tables and Figures, each composition of the present invention may be characterized by any one, any two, any three, any four, any five, any six, any seven, or any eight or more of the 2 theta angle peaks. Any one, two, three, four, five, or six DSC transitions can also be used to characterize the compositions of the present invention. The different combinations of the PXRD peaks and the DSC transitions can also be used to characterize the compositions.

Example 1

Modafinil:Succinic Acid:Fumaric Acid Mixed Co-Crystals

Grinding experiments were carried out in stainless steel milling apparatuses (Wig-L-Bug containers) to determine the effect of varying the fumaric acid content in modafinil:succinic acid:fumaric acid mixed co-crystals. The target mole ratio of [modafinil]:[succinic acid]:[fumaric acid] was [2]:[1-X]:[X], with X being the mole fraction of fumaric acid and varied from 0.0 to 1.0 in 0.1 increments. Samples were ground in the presence of acetone (40 percent by volume) then allowed to dry in air. Analysis by PXRD showed that for all samples complete conversion to the co-crystal was seen except for the 0.9 and 1.0 fumaric acid mole fraction samples. Additional 0.9 and 1.0 fumaric acid samples were weighed then wet ground (with acetone) while sealed with parafilm in order to prevent the loss of powder during grinding. PXRD analysis of the 0.9 fumaric acid mole fraction sample showed additional conversion but modafinil form 2 peaks remained (there were no form 1 peaks seen, although the modafinil starting material is a mixture of mostly form 2 and some form 1). Analysis of the 1.0 fumaric acid mole fraction sample still showed no formation of the co-crystal after drying. The sample was wet ground again with 66% v/v acetone and resulted in the formation of the co-crystal along with conversion of the modafinil to form 1. The mixed modafinil:succinic acid:fumaric acid co-crystals (0.0 to 1.0 fumaric acid mole fraction) were analyzed by PXRD and DSC.

The mixed co-crystals may be expressed in terms of (fumaric acid) mole fraction or in a percentage (fumaric acid) of the total amount of co-crystal former present in the mixed co-crystal. For example, a mixed co-crystal with a stoichiometry of $[modafinil]_2:[succinic\ acid]_{0.9}:[fumaric\ acid]_{0.1}$ may be described as having a 0.1 fumaric acid mole fraction, or as a 10% fumaric acid mixed co-crystal.

TABLE 1

Composition of modafinil:succinic acid:fumaric acid samples

| % Mol Fumaric acid (Target) | Modafinil (mg) | Succinic acid (mg) | Fumaric acid (mg) | Moles Modafinil | Moles Succinic acid | Moles Fumaric acid |
|---|---|---|---|---|---|---|
| 0 | 246.60 | 53.90 | 0.00 | 0.902 | 0.456 | 0.000 |
| 10 | 247.60 | 49.00 | 5.80 | 0.906 | 0.415 | 0.050 |
| 20 | 244.50 | 43.70 | 11.40 | 0.894 | 0.370 | 0.098 |
| 30 | 247.60 | 39.60 | 15.70 | 0.906 | 0.335 | 0.135 |
| 40 | 248.60 | 32.40 | 21.10 | 0.909 | 0.274 | 0.182 |
| 50 | 245.80 | 29.30 | 27.70 | 0.899 | 0.248 | 0.239 |
| 60 | 246.50 | 22.90 | 32.40 | 0.902 | 0.194 | 0.279 |
| 70 | 246.60 | 17.00 | 36.80 | 0.902 | 0.144 | 0.317 |
| 80 | 246.50 | 11.10 | 41.90 | 0.902 | 0.094 | 0.361 |
| 90 | 247.10 | 5.70 | 47.36 | 0.904 | 0.048 | 0.408 |
| 100 | 247.60 | 0.00 | 54.40 | 0.906 | 0.000 | 0.469 |

TABLE 2

Composition of modafinil:succinic acid:fumaric acid samples

| % Mol Fumaric | Mol frac Modafinil | Mol frac Succinic | Mol frac Fumaric | % Mol Fumaric of CCF | 2:x | Weight % Modafinil | Weight % Succinic | Weight % Fumaric |
|---|---|---|---|---|---|---|---|---|
| 0 | 0.664 | 0.336 | 0.000 | 0.00 | 1.012 | 82.06 | 17.94 | 0.00 |
| 10 | 0.661 | 0.303 | 0.036 | 10.75 | 1.026 | 81.88 | 16.20 | 1.92 |
| 20 | 0.656 | 0.272 | 0.072 | 20.97 | 1.047 | 81.61 | 14.59 | 3.81 |
| 30 | 0.658 | 0.244 | 0.098 | 28.74 | 1.039 | 81.74 | 13.07 | 5.18 |
| 40 | 0.666 | 0.201 | 0.133 | 39.85 | 1.003 | 82.29 | 10.72 | 6.98 |
| 50 | 0.649 | 0.179 | 0.172 | 49.03 | 1.083 | 81.18 | 9.68 | 9.15 |
| 60 | 0.656 | 0.141 | 0.203 | 59.01 | 1.049 | 81.68 | 7.59 | 10.74 |
| 70 | 0.662 | 0.106 | 0.233 | 68.77 | 1.022 | 82.09 | 5.66 | 12.25 |
| 80 | 0.665 | 0.069 | 0.266 | 79.34 | 1.009 | 82.30 | 3.71 | 13.99 |
| 90 | 0.665 | 0.035 | 0.300 | 89.42 | 1.009 | 82.32 | 1.90 | 15.78 |
| 100 | 0.659 | 0.000 | 0.341 | 100.00 | 1.035 | 81.99 | 0.00 | 18.01 |

Figure 2:
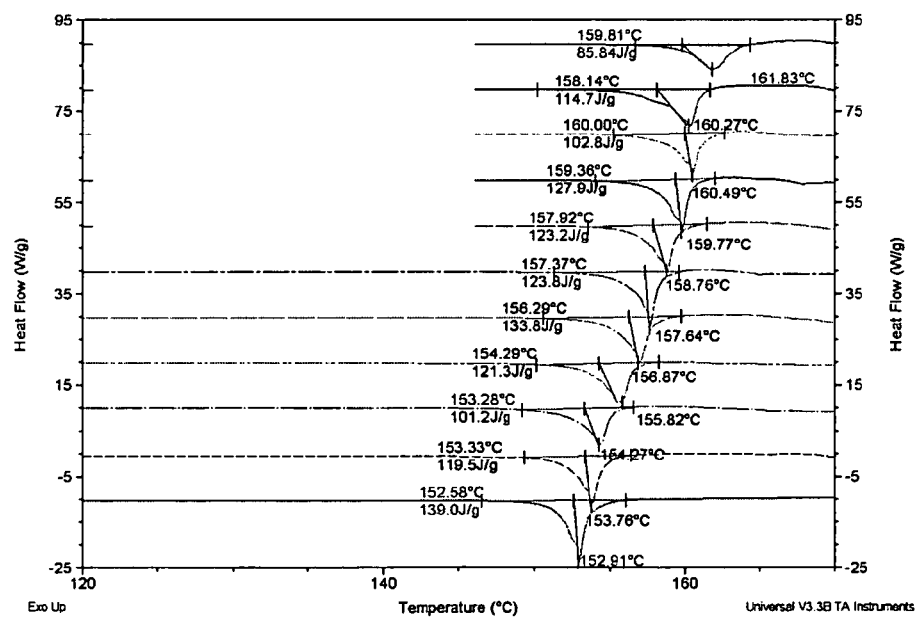
FIG. 2 shows an overlay of 11 DSC thermograms of the modafinil:succinic acid co-crystal, the modafinil:fumaric acid co-crystal, and nine mixed co-crystals (0.1-0.9 fumaric acid mole fraction, in increments of 0.1)

FIG. 1 shows an overlay of 11 PXRD diffractograms of the modafinil:succinic acid co-crystal, the modafinil:fumaric acid co-crystal, and nine mixed co-crystals (0.1-0.9 fumaric acid mole fraction, in increments of 0.1). In FIG. 1, the top diffractrogram is the parent co-crystal modafinil:fumaric acid and the bottom diffractogram is the parent co-crystal modafinil:succinic acid. The intermediate diffractograms are of the mixed modafinil:succinic acid:fumaric acid co-crystals in increments of 0.1 mole fraction. FIG. 2 shows an overlay of 11 DSC thermograms of the modafinil:succinic acid co-crystal, the modafinil:fumaric acid co-crystal, and nine mixed co-crystals (0.1-0.9 fumaric acid mole fraction, in increments of 0.1). In FIG. 2, the top thermogram is the parent co-crystal modafinil:fumaric acid and the bottom thermogram is the parent co-crystal modafinil:succinic acid. The intermediate thermograms are of the mixed modafinil:succinic acid:fumaric acid co-crystals in increments of 0.1 mole fraction.

Figure 3:
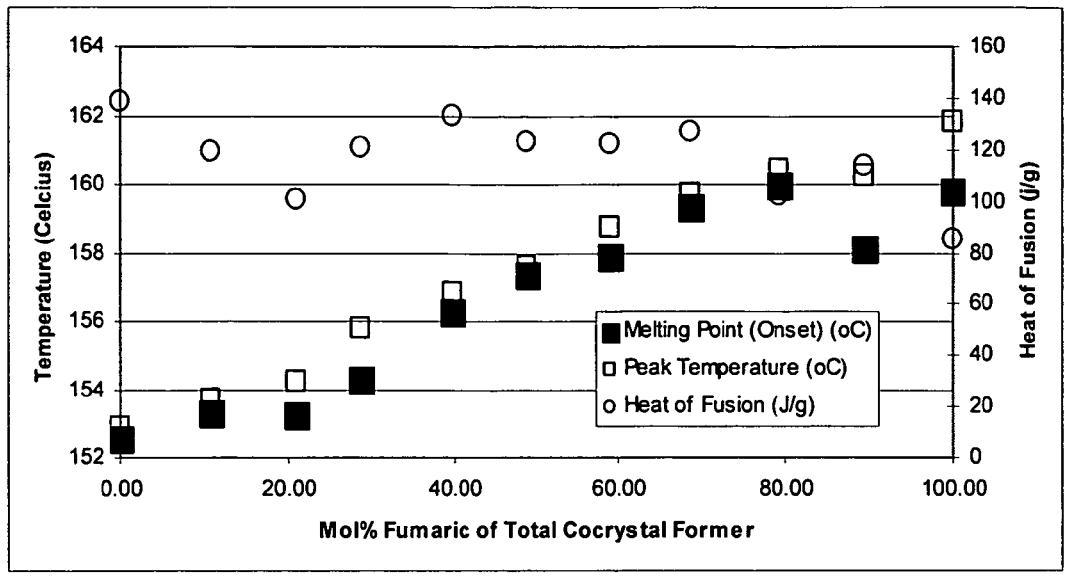
FIG. 3 shows the melting points, heats of fusion, and peak temperature as a function of mole percent fumaric acid for the modafinil:succinic acid:fumaric acid mixed co-crystals
Figure 4:
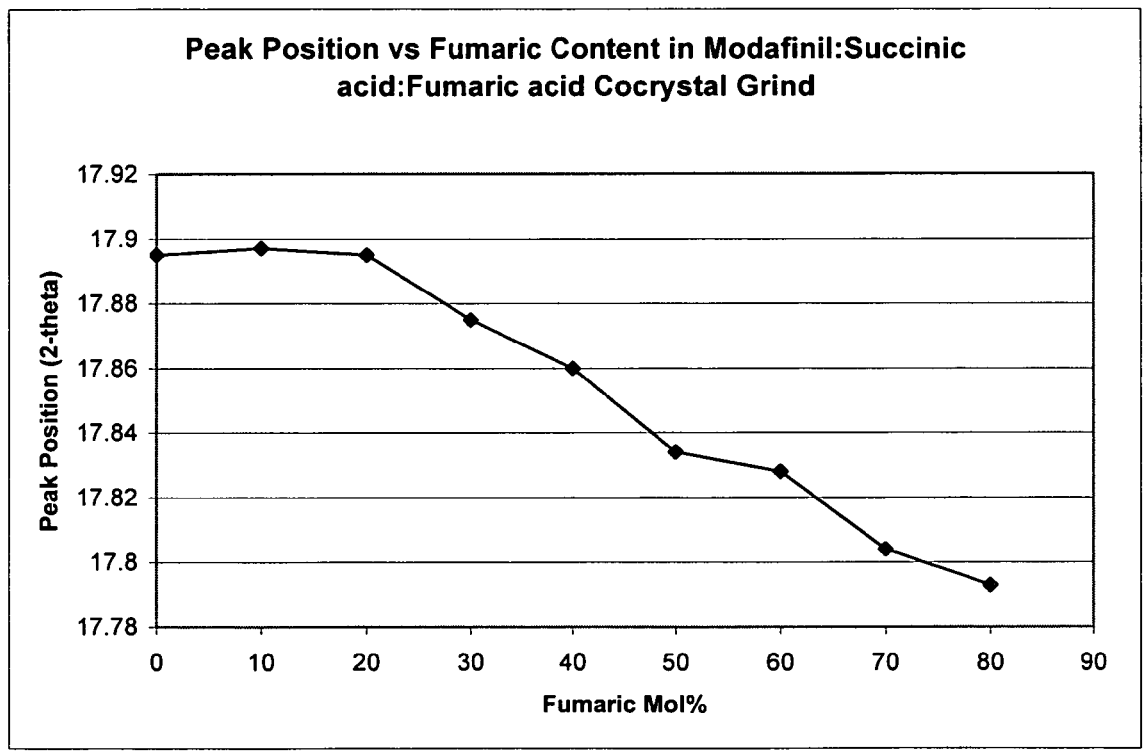
FIG. 4 shows a shift in peak position of the modafinil:succinic acid PXRD peak found near 17.9 degrees 2-theta as the mole percent of fumaric acid is increased
Figure 5:
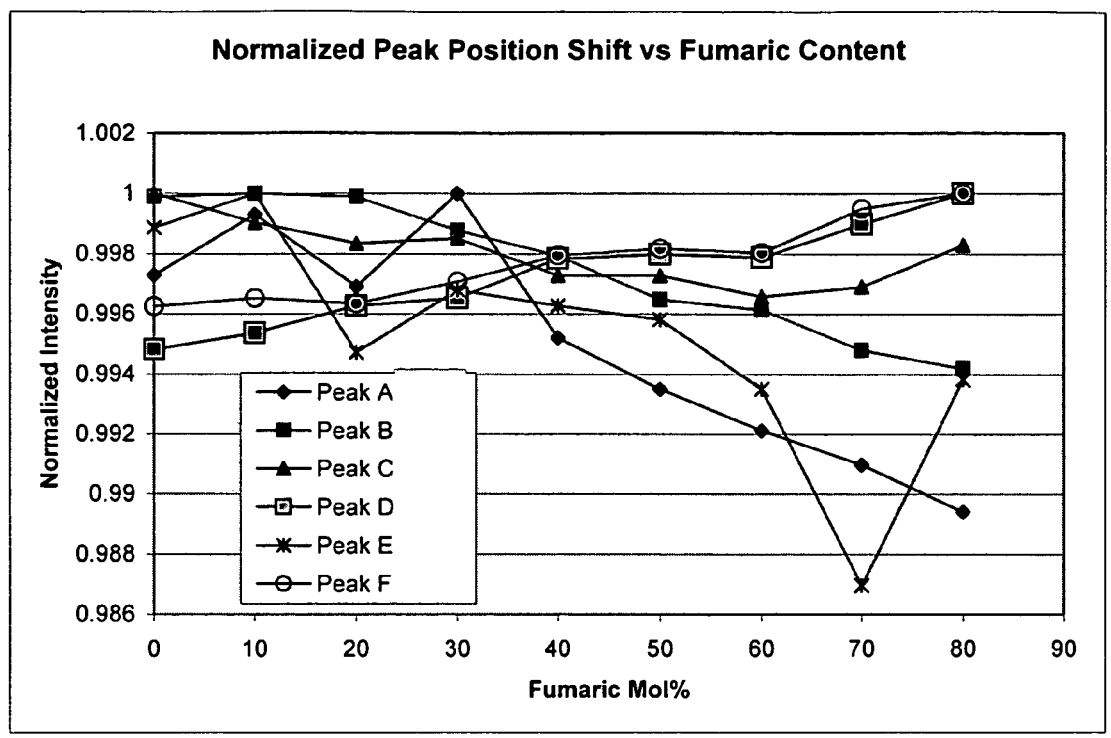
FIG. 5 shows the normalized peak positions of six modafinil:succinic acid PXRD peaks (15.8, 17.9, 18.8, 19.8, 21.2, and 21.8 degrees 2-theta) as the mole percent of fumaric acid is increased
Figure 6:
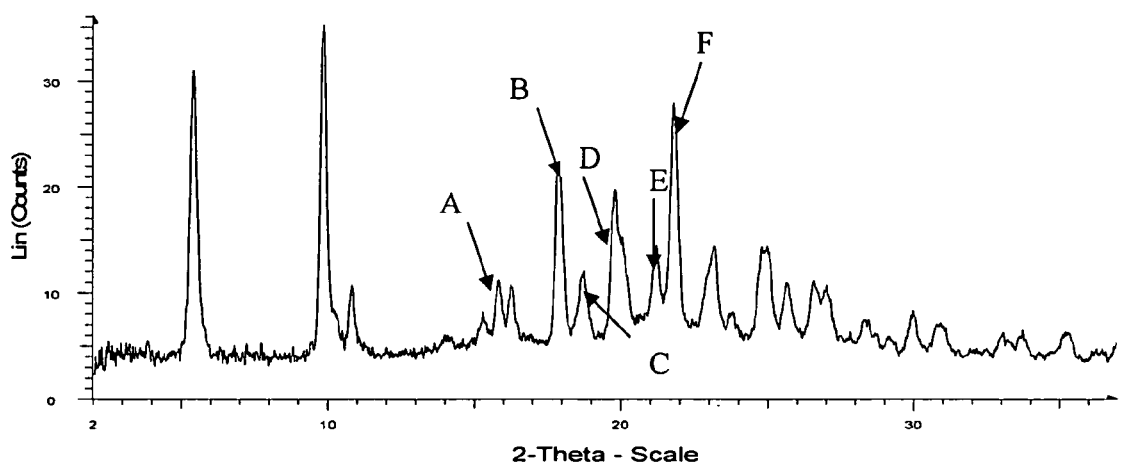
FIG. 6 shows a PXRD diffractogram of modafinil:succinic acid with the six peaks of interest from FIG. 5 labelled (A-F).
Figure 7:
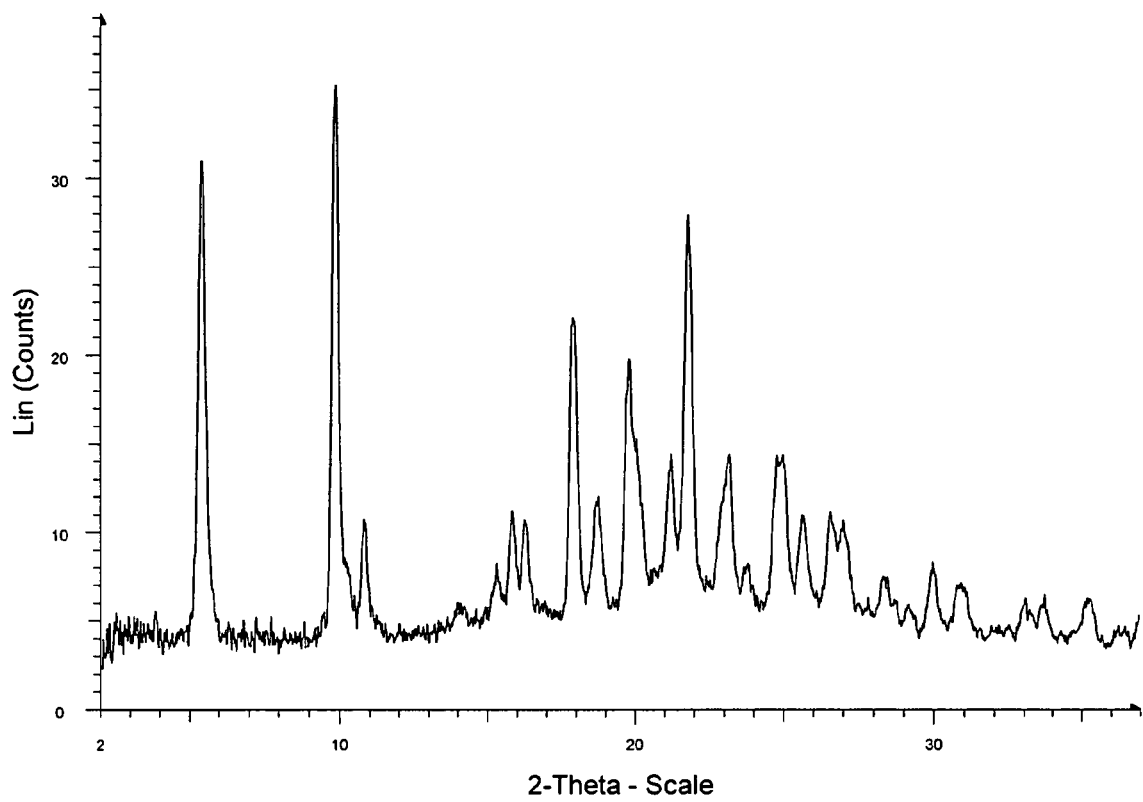
FIG. 7 shows a PXRD diffractogram of a modafinil:succinic acid co-crystal.

FIG. 3 shows the melting points, heats of fusion, and peak temperature as a function of mole percent fumaric acid for the modafinil:succinic acid:fumaric acid mixed co-crystals. FIG. 4 shows a shift in peak position of the modafinil:succinic acid PXRD peak found near 17.9 degrees 2-theta as the mole percent of fumaric acid is increased. FIG. 5 shows the normalized peak positions of six modafinil:succinic acid PXRD peaks (A=15.87, B=17.99, C=18.75, D=19.95, E=21.35, and F=21.95 degrees 2-theta) as the mole percent of fumaric acid is increased. FIG. 6 shows a PXRD diffractogram of modafinil:succinic acid with the six peaks of interest from FIG. 5 labelled (A-F).

FIGS. 7-17 show PXRD diffractograms of the nine modafinil mixed co-crystals and both parent co-crystals described above. The 1:1 modafinil:succinic acid co-crystals can be characterized by any one, any two, any three, any four, any five, or any six or more of the peaks in FIG. 7 including, but not limited to, 5.35, 9.81, 10.78, 15.82, 16.27, 17.89, 18.71, 19.79, 21.22, 21.81, 23.17, 24.83, 25.67, 26.59, 27.07, 30.02, 30.89, and 35.34 degrees 2-theta (Bruker, as collected). The 1:0.9:0.1 modafinil:succinic acid:fumaric acid mixed co-crystal can be characterized by any one, any two, any three, any four, any five, or any six or more of the peaks in FIG. 8 including, but not limited to, 5.35, 9.81, 10.77, 15.32, 15.81, 16.27, 17.90, 18.74, 19.81, 20.06, 21.23, 21.82, 23.18, 24.79, 24.99, 25.66, 26.61, 27.07, 28.39, 30.01, 30.91, 31.07,

TABLE 3

Melting points, Heats of fusion data for mixed co-crystals

| Mol % Fumaric Acid (of total CCF) | Melting Point (° C.) | Heat of Fusion (J/g) | Peak Temperature (° C.) | Actual Mol % Fumaric Acid | Actual Modafinil:CCF Ratio (2:X) |
|---|---|---|---|---|---|
| 0 | 152.58 | 139.0 | 152.91 | 0.00 | 1.012 |
| 10 | 153.33 | 119.5 | 153.76 | 10.75 | 1.026 |
| 20 | 153.28 | 101.2 | 154.27 | 20.97 | 1.047 |
| 30 | 154.29 | 121.3 | 155.82 | 28.74 | 1.039 |
| 40 | 156.29 | 133.8 | 156.87 | 39.85 | 1.003 |
| 50 | 157.37 | 123.8 | 157.64 | 49.03 | 1.083 |
| 60 | 157.92 | 123.2 | 158.76 | 59.01 | 1.049 |
| 70 | 159.36 | 127.9 | 159.77 | 68.77 | 1.022 |
| 80 | 160.0 | 102.8 | 160.49 | 79.34 | 1.009 |
| 90* | 158.14 | 114.7 | 160.27 | 89.42 | 1.009 |
| 100** | 159.81 | 85.84 | 161.83 | 100.00 | 1.035 |

*PXRD pattern shows some modafinil peaks
**From separate experiment 33.08, 33.80, and 35.39 degrees 2-theta (Bruker, as collected). The 1:0.8:0.2 modafinil:succinic acid:fumaric acid mixed co-crystal can be characterized by any one, any two, any three, any four, any five, or any six or more of the peaks in FIG. 9 including, but not limited to, 5.36, 9.82, 10.77, 15.30, 15.82, 16.27, 17.89, 18.73, 19.82, 21.19, 21.81, 23.12, 23.79, 25.01, 25.69, 26.64, 27.08, 29.99, 30.93, 33.76, and 35.29 degrees 2-theta (Bruker, as collected). The 1:0.7:0.3 modafinil:succinic acid:fumaric acid mixed co-crystal can be characterized by any one, any two, any three, any four, any five, or any six or more of the peaks in FIG. 10 including, but not limited to, 5.37, 9.81, 10.78, 15.30, 15.80, 16.28, 17.87, 18.73, 19.83, 21.18, 21.83, 23.14, 23.82, 24.80, 25.04, 25.71, 26.63, 27.10, 30.01, 30.99, 33.12, 33.78, and 35.32 degrees 2-theta (Bruker, as collected). The 1:0.6:0.4 modafinil:succinic acid:fumaric acid mixed co-crystal can be characterized by any one, any two, any three, any four, any five, or any six or more of the peaks in FIG. 11 including, but not limited to, 5.36, 9.83, 10.79, 15.32, 15.78, 16.29, 17.86, 18.71, 19.85, 21.16, 21.85, 23.18, 23.81, 24.81, 25.74, 26.65, 27.11, 28.42, 30.01, 31.04, 33.14, 33.81, and 35.30 degrees 2-theta (Bruker, as collected). The 1:0.5:0.5 modafinil:succinic acid:fumaric acid mixed co-crystal can be characterized by any one, any two, any three, any four, any five, or any six or more of the peaks in FIG. 12 including, but not limited to, 5.37, 9.83, 10.81, 15.32, 15.76, 16.29, 17.83, 18.71, 19.85, 20.04, 21.16, 21.86, 23.19, 23.80, 24.81, 25.01, 25.69, 26.66, 27.08, 28.43, 29.26, 30.00, 31.04, and 33.79 degrees 2-theta (Bruker, as collected). The 1:0.4:0.6 modafinil:succinic acid:fumaric acid mixed co-crystal can be characterized by any one, any two, any three, any four, any five, or any six or more of the peaks in FIG. 13 including, but not limited to, 5.37, 9.83, 10.79, 15.32, 15.73, 16.31, 17.83, 18.71, 19.85, 20.18, 21.11, 21.85, 23.14, 23.85, 24.80, 25.04, 25.73, 26.64, 27.14, 29.24, 29.95, 31.02, 33.16, 33.79, and 35.19 degrees 2-theta (Bruker, as collected). The 1:0.3:0.7 modafinil:succinic acid:fumaric acid mixed co-crystal can be characterized by any one, any two, any three, any four, any five, or any six or more of the peaks in FIG. 14 including, but not limited to, 5.38, 9.86, 10.81, 14.10, 15.36, 15.73, 16.32, 17.81, 18.70, 19.89, 20.97, 21.89, 23.20, 24.94, 25.72, 26.67, 27.13, 28.47, 29.99, 31.06, 33.16, 33.82, and 35.05 degrees 2-theta (Bruker, as collected). The 1:0.2:0.8 modafinil:succinic acid:fumaric acid mixed co-crystal can be characterized by any one, any two, any three, any four, any five, or any six or more of the peaks in FIG. 15 including, but not limited to, 5.38, 9.85, 10.82, 15.69, 16.33, 17.79, 18.73, 19.90, 20.08, 21.12, 21.89, 23.24, 24.82, 25.03, 25.74, 26.68, 27.16, 28.60, 30.02, 31.07, 33.87, and 35.10 degrees 2-theta (Bruker, as collected). The 1:0.1:0.9 modafinil:succinic acid:fumaric acid mixed co-crystal can be characterized by any one, any two, any three, any four, any five, or any six or more of the peaks in FIG. 16 including, but not limited to, 5.37, 8.92, 9.85, 10.81, 12.77, 15.66, 16.31, 17.73, 18.72, 19.18, 19.90, 20.22, 21.09, 21.91, 23.07, 23.80, 24.73, 25.03, 25.77, 26.67, 27.15, 28.53, 29.95, 31.06, and 35.10 degrees 2-theta (Bruker, as collected). The 1:1 modafinil:fumaric acid co-crystal (form I) can be characterized by any one, any two, any three, any four, any five, or any six or more of the peaks in FIG. 17 including, but not limited to, 5.37, 9.85, 10.83, 15.68, 16.35, 17.74, 18.69, 19.92, 21.09, 21.89, 23.07, 23.79, 24.73, 25.02, 25.76, 26.73, 27.14, 28.53, 31.01, 33.22, and 35.05 degrees 2-theta (Bruker, as collected).

(Comparative) Example 2

Modafinil:Succinic Acid and Modafinil:Fumaric Acid Co-crystals

Figure 18:
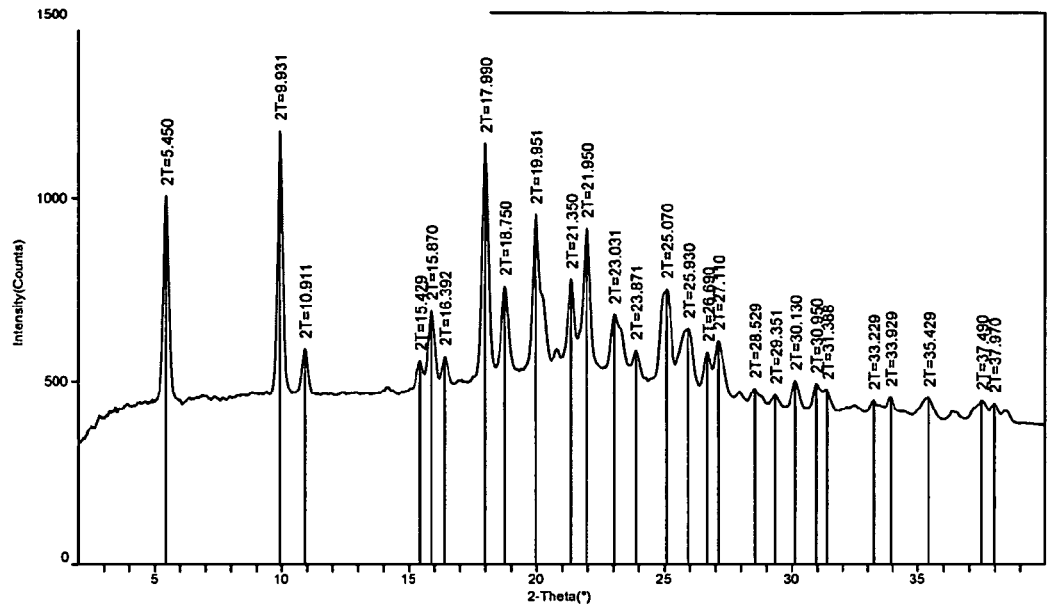
FIG. 18 shows a PXRD diffractogram of modafinil:succinic acid.
Figure 19:
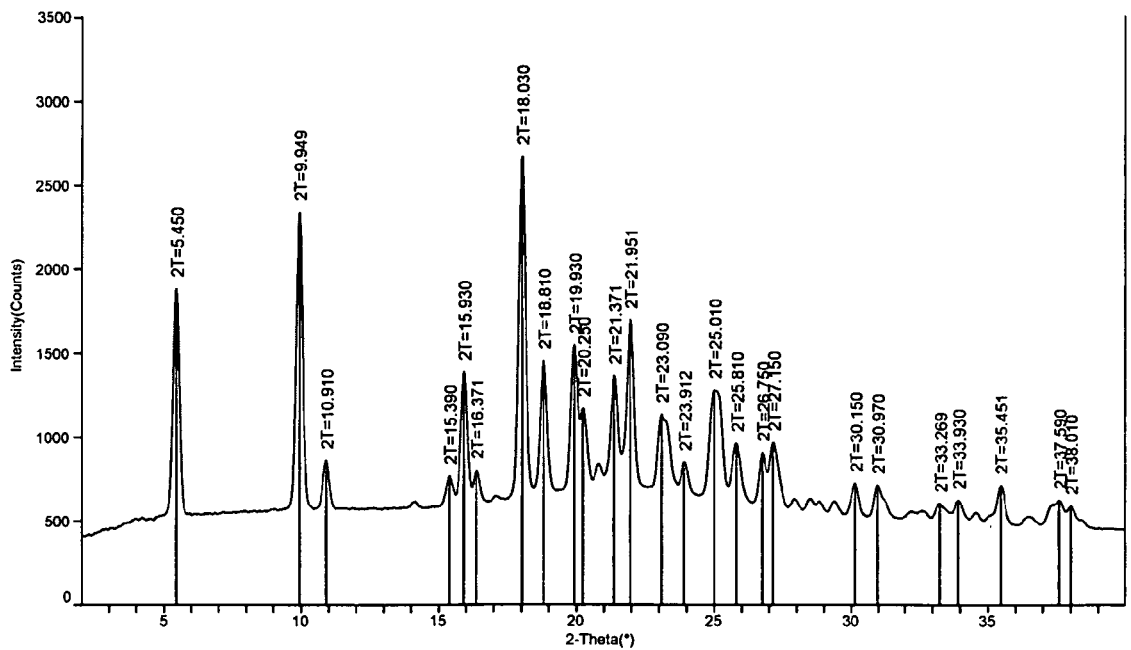
FIG. 19 shows a PXRD diffractogram of modafinil:fumaric acid (form I).

FIG. 18 shows a PXRD diffractogram of modafinil:succinic acid. FIG. 19 shows a PXRD diffractogram of modafinil:fumaric acid (form I).

Example 3

Urea:5-Fluorouracil:Uracil Mixed Co-Crystals

Grinding experiments were carried out to determine the effect of varying the uracil content in urea:5-fluorouracil:uracil mixed co-crystals. The target mole ratio of [urea]:[5-fluorouracil]:[uracil] was [1]:[1-X]:[X], with X being the mole fraction of uracil and varied from 0.0 to 1.0 in 0.1 increments.

A 1:1 urea:uracil co-crystal was prepared according to the following method. To urea (10 mg, 0.1665 mmol) was added uracil (18.6 mg, 0.1665 mmol). The mixture was then ground for 10 minutes and characterized using PXRD.

A 1:0.1:0.9 urea:5-fluorouracil:uracil mixed co-crystal was prepared according to the following method. To urea (10.1 mg, 0.1665 mmol) was added uracil (16.6 mg, 0.1499 mmol) and 5-fluorouracil (2.3 mg, 0.01665 mmol). The mixture was then ground for 10 minutes and characterized using PXRD. A similar procedure was carried out for mixtures containing 80, 70, 60, 50, 40, 30, 20, and 10 moll percent uracil.

A 1:1 urea:5-fluorouracil co-crystal was prepared according to the following method. To urea (10.1 mg, 0.1665 mmol) was added 5-fluorouracil (21.9 mg, 0.1665 mmol). The mixture was then ground for 10 minutes and characterized using PXRD.

Figure 20:
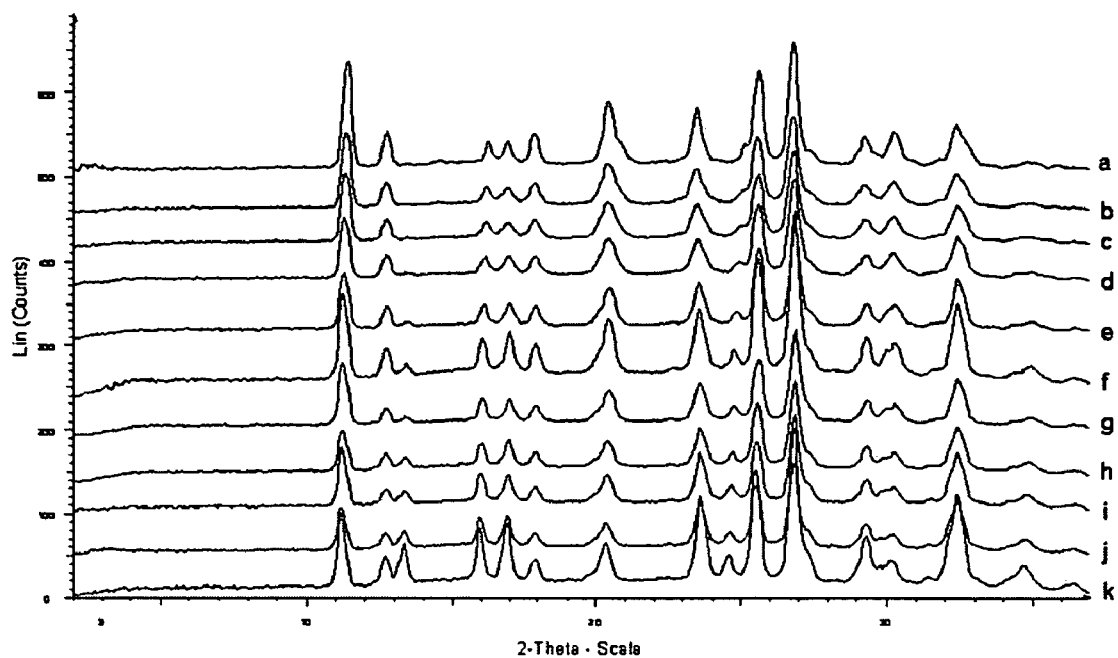
FIG. 20 shows an overlay of PXRD diffractograms from grinding uracil and 5-fluorouracil with urea.

FIG. 20 shows an overlay of powder patterns obtained from grinding mixed compositions of uracil and 5-fluorouracil with urea. In FIG. 20, a. 1:1 urea:uracil co-crystal; b. 1:0.1:0.9 urea:5-fluorouracil:uracil mixed co-crystal; c. 1:0.2:0.8 urea:5-fluorouracil: uracil mixed co-crystal; d. 1:0.3:0.7 urea:5-fluorouracil:uracil mixed co-crystal; e. 1:0.4:0.6 urea:5-fluorouracil:uracil mixed co-crystal; f. 1:0.5:0.5 urea:5-fluorouracil:uracil mixed co-crystal; g. 1:0.6:0.4 urea:5-fluorouracil:uracil mixed co-crystal; h. 1:0.7:0.3 urea:5-fluorouracil:uracil mixed co-crystal; i. 1:0.8:0.2 urea:5-fluorouracil:uracil mixed co-crystal; j. 1:0.9:0.1 urea:5-fluorouracil:uracil mixed co-crystal; and k. 1:1 urea:5-fluorouracil co-crystal.

Table 4 shows the materials used for the synthesis of urea mixed co-crystals and their respective percent compositions (with respect to the co-crystal formers).

TABLE 4

Materials used for Grinding Screen

| % Composition | Compound | MW (g/mol) | Amount (mg) | Mol (mmol) |
|---|---|---|---|---|
| 100% Uracil | Urea | 60.06 | 10.0 | 0.1665 |
| | Uracil | 112.09 | 18.6 | 0.1659 (100%) |
| 90% Uracil | Urea | 60.06 | 10.1 | 0.1682 |
| | Uracil | 112.09 | 16.6 | 0.1481 (88%) |
| | 5-Fluorouracil | 130.08 | 2.3 | 0.0177 (10.5%) |
| 80% Uracil | Urea | 60.06 | 9.9 | 0.1648 |
| | Uracil | 112.09 | 14.9 | 0.1329 (80.6%) |
| | 5-Fluorouracil | 130.08 | 4.2 | 0.0323 (19.6%) |
| 70% Uracil | Urea | 60.06 | 9.9 | 0.1648 |
| | Uracil | 112.09 | 12.9 | 0.1151 (69.8%) |
| | 5-Fluorouracil | 130.08 | 6.4 | 0.0492 (29.9%) |
| 60% Uracil | Urea | 60.06 | 9.9 | 0.1648 |
| | Uracil | 112.09 | 11 | 0.0981 (59.5%) |
| | 5-Fluorouracil | 130.08 | 8.7 | 0.0669 (40.6%) |
| 50% Uracil | Urea | 60.06 | 10 | 0.1665 |
| | Uracil | 112.09 | 9.3 | 0.0830 (49.8%) |
| | 5-Fluorouracil | 130.08 | 10.9 | 0.0838 (50.3%) |
| 40% Uracil | Urea | 60.06 | 9.9 | 0.1648 |
| | Uracil | 112.09 | 8.1 | 0.0723 (43.9%) |
| | 5-Fluorouracil | 130.08 | 12.7 | 0.0976 (59.2%) |

TABLE 4-continued

Materials used for Grinding Screen

| % Composition | Compound | MW (g/mol) | Amount (mg) | Mol (mmol) | |
|---|---|---|---|---|---|
| 30% Uracil | Urea | 60.06 | 9.8 | 0.1632 | |
| | Uracil | 112.09 | 5.5 | 0.0491 | (30.1%) |
| | 5-Fluorouracil | 130.08 | 15.2 | 0.1169 | (71.6%) |
| 20% Uracil | Urea | 60.06 | 9.8 | 0.1632 | |
| | Uracil | 112.09 | 3.6 | 0.0321 | (19.7%) |
| | 5-Fluorouracil | 130.08 | 17.2 | 0.1322 | (81%) |
| 10% Uracil | Urea | 60.06 | 9.9 | 0.1648 | |
| | Uracil | 112.09 | 1.7 | 0.0152 | (9.2%) |
| | 5-Fluorouracil | 130.08 | 19.5 | 0.1499 | (91%) |
| 100% 5-Fluorouracil | Urea | 60.06 | 10.1 | 0.1682 | |
| | 5-Fluorouracil | 130.08 | 21.9 | 0.1684 | (100%) |

Figure 21:
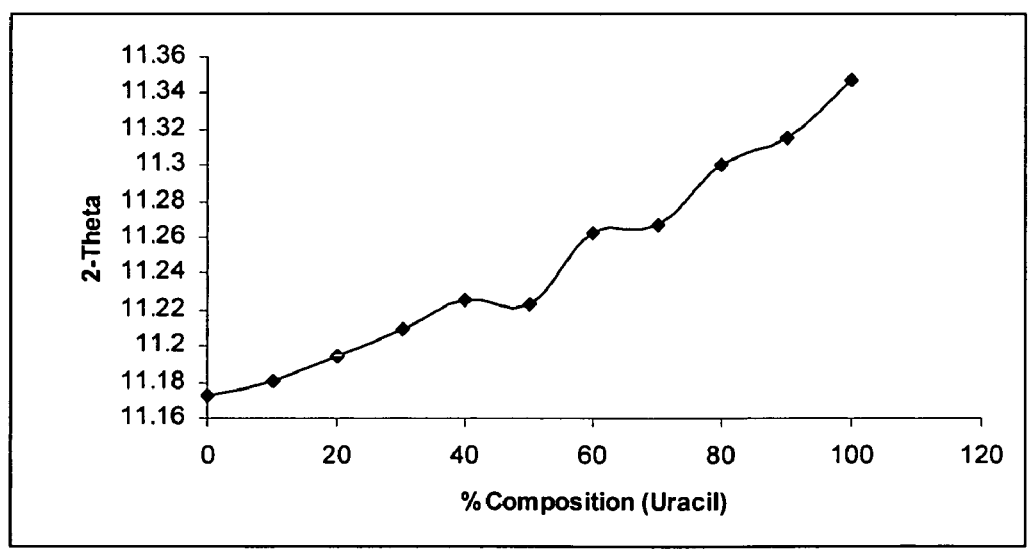
FIG. 21 shows a plot of the PXRD peak position at ~11 degrees 2-theta versus the percent composition (uracil) of the mixed co-crystal.

Table 5 and FIG. 21 show the shifting position of a peak at about 11.35 degrees 2-theta of the urea:uracil parent co-crystal.

TABLE 5

Composition of mixed co-crystals versus 2-theta

| Composition (%) | 2-Theta (deg) |
|---|---|
| 1:1 Urea:5-fluorouracil | 11.173 |
| 1:0.9:0.1 urea:5-fluorouracil:uracil | 11.181 |
| 1:0.8:0.2 urea:5-fluorouracil:uracil | 11.195 |
| 1:0.7:0.3 urea:5-fluorouracil:uracil | 11.21 |
| 1:0.6:0.4 urea:5-fluorouracil:uracil | 11.226 |
| 1:0.5:0.5 urea:5-fluorouracil:uracil | 11.223 |
| 1:0.4:0.6 urea:5-fluorouracil:uracil | 11.262 |
| 1:0.3:0.7 urea:5-fluorouracil:uracil | 11.267 |
| 1:0.2:0.8 urea:5-fluorouracil:uracil | 11.3 |
| 1:0.1:0.9 urea:5-fluorouracil:uracil | 11.315 |
| 1:1 Urea:uracil | 11.347 |

Figure 22:
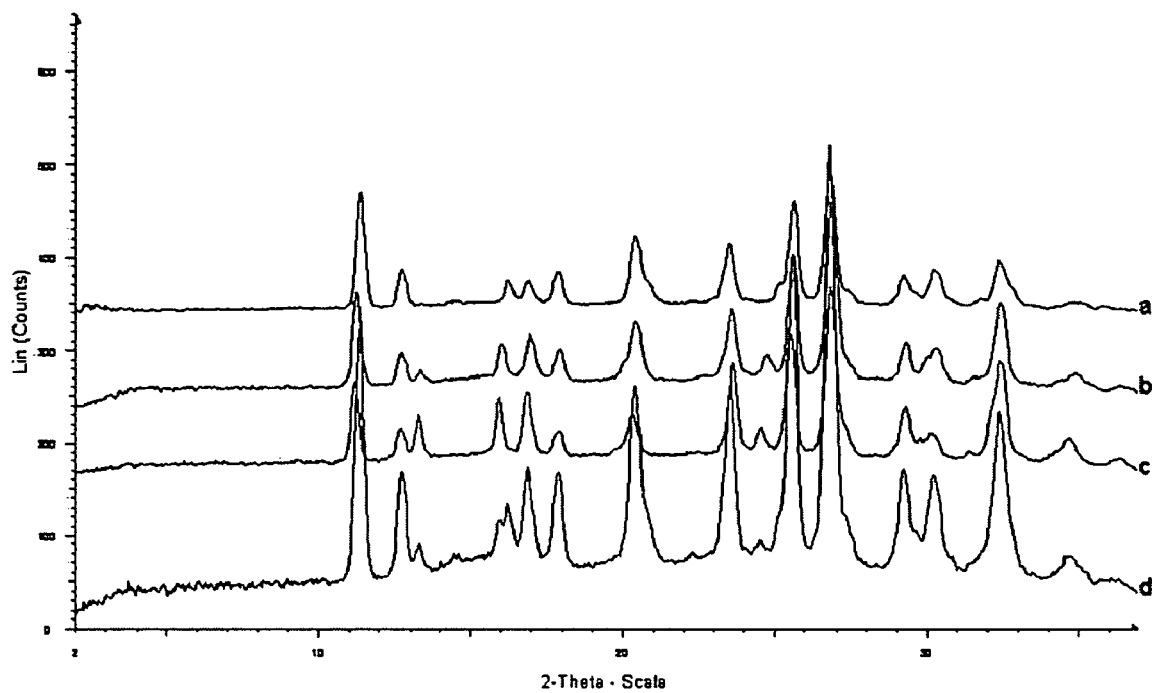
FIG. 22 shows a comparison of PXRD diffractograms of two parent co-crystals, a mixed co-crystal, and a physical mixture of co-crystals.

FIG. 21 shows a gradual increase in 2-theta as the composition of uracil is increased, with the exception when the composition is 1:0.5:0.5 urea:5-fluorouracil:uracil. (FIG. 21 shows mixed co-crystals as a percent composition of uracil. 100 percent=all uracil co-crystal former, 50 percent=50 percent uracil co-crystal former and 50 percent 5-fluorouracil co-crystal former, 0 percent=all 5-fluorouracil co-crystal former) In order to determine if the mixed co-crystal 1:0.5:0.5 urea:5-fluorouracil:uracil is a physical mixture of the two corresponding parent co-crystals, 1:1 urea:uracil:urea and 1:1 urea:5-fluorouracil co-crystals were prepared. A physical mixture containing 50% of each parent co-crystal was then prepared and characterized using PXRD. FIG. 22 illustrates an overlay of the two parent co-crystals, the 1:0.5:0.5 urea:5-fluorouracil:uracil mixed co-crystal and a physical mixture of the 1:1 urea:uracil and 1:1 urea:5-fluorouracil co-crystals.

FIG. 22 includes: a. 1:1 urea:uracil co-crystal; b. 1:0.5:0.5 urea:5-fluorouracil:uracil mixed co-crystal; c. 1:1 urea:5-fluorouracil co-crystal; and d. physical mixture containing 1:1 urea:uracil co-crystal and 1:1 urea:5-fluorouracil co-crystal.

Analysis of the powder patterns from FIG. 22 indicates that the doublet of the peak at ~16 degrees 2-theta in the physical mixture (pattern d from FIG. 22) is not present in the 1:0.5:0.5 urea:5-fluorouracil:uracil mixed co-crystal (spectrum b from FIG. 22) indicating that the mixed co-crystal is not a physical mixture of the two parent co-crystals.

Figure 23:
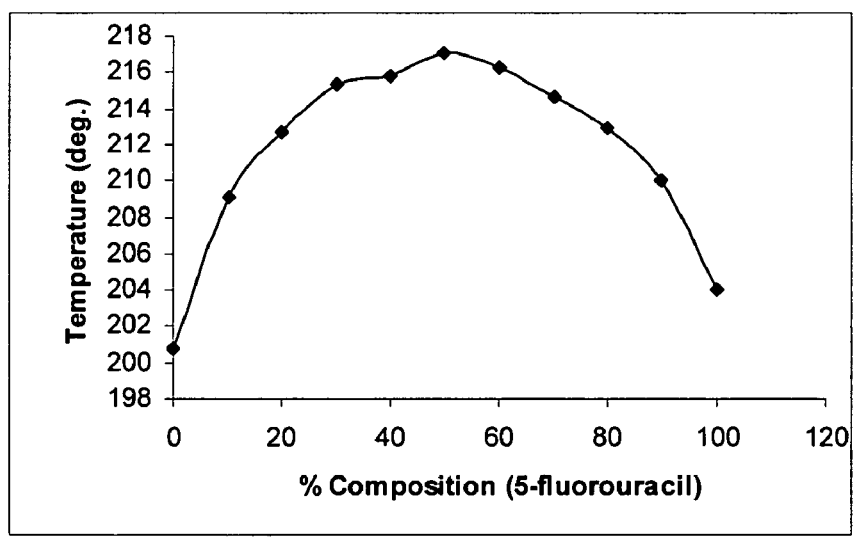
FIG. 23 shows a plot of endotherms observed in mixed co-crystals versus the percent composition (5-fluorouracil).
Figure 24:
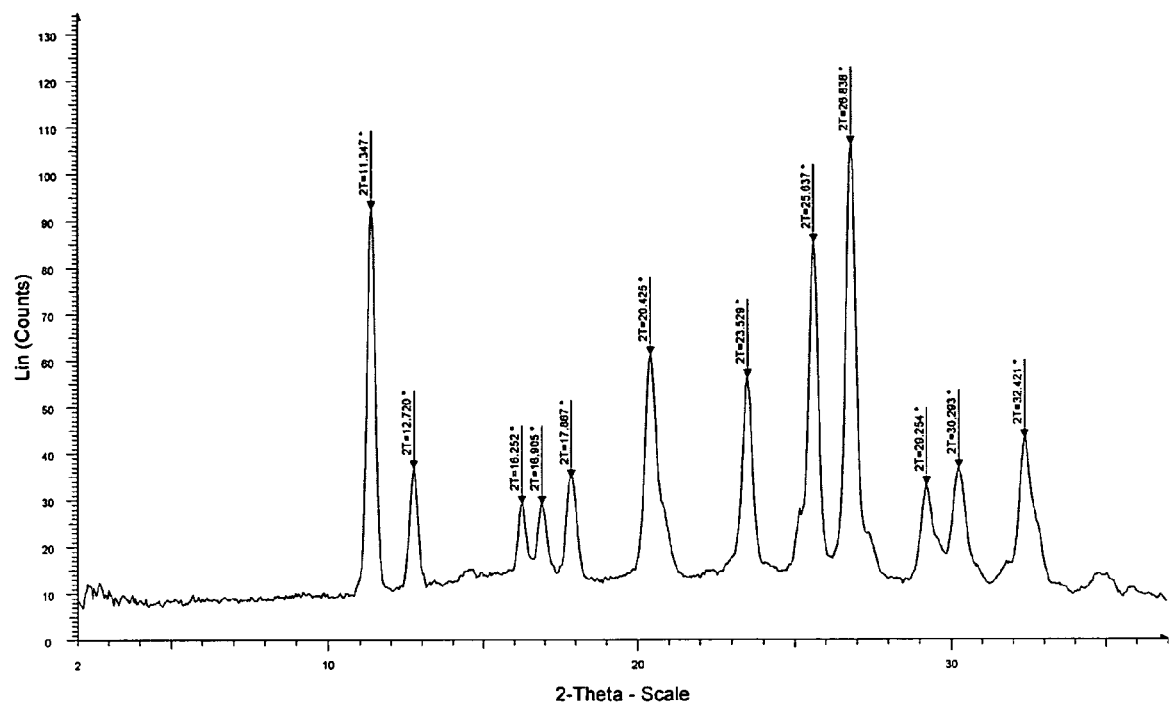
FIG. 24 shows a PXRD diffractogram of the urea:uracil parent co-crystal.
Figure 25:
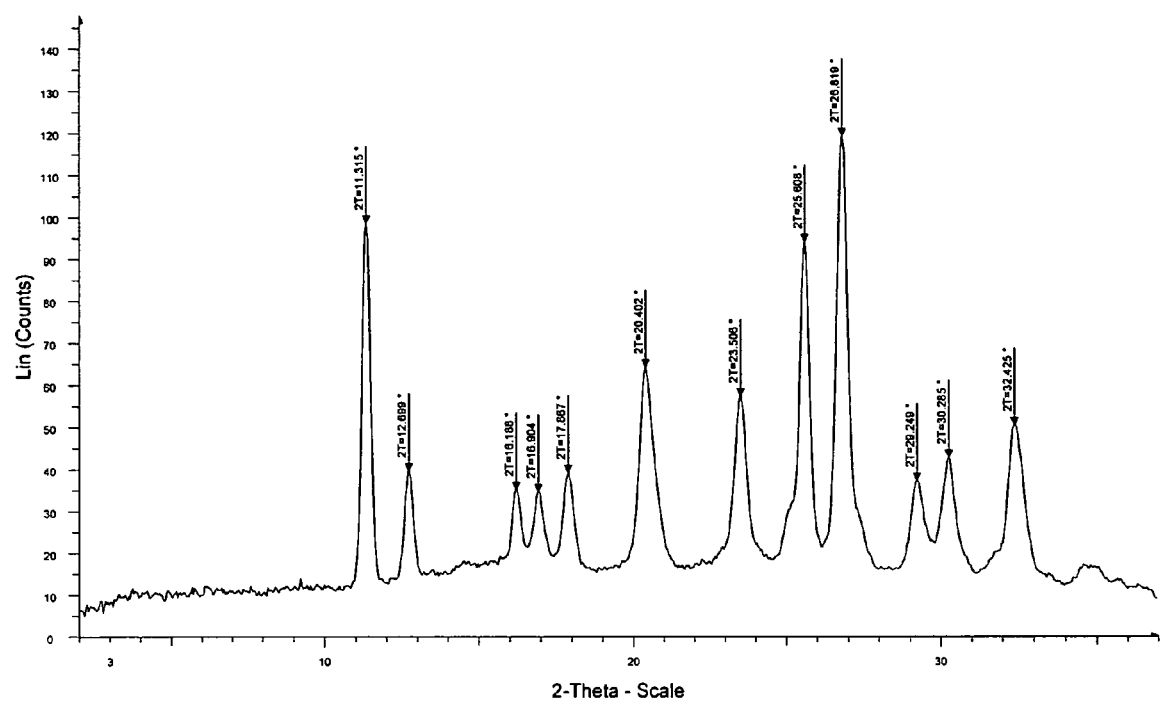
FIG. 25 shows a PXRD diffractogram of a 1:0.1:0.9 urea:5-fluorouracil:uracil mixed co-crystal.
Figure 26:
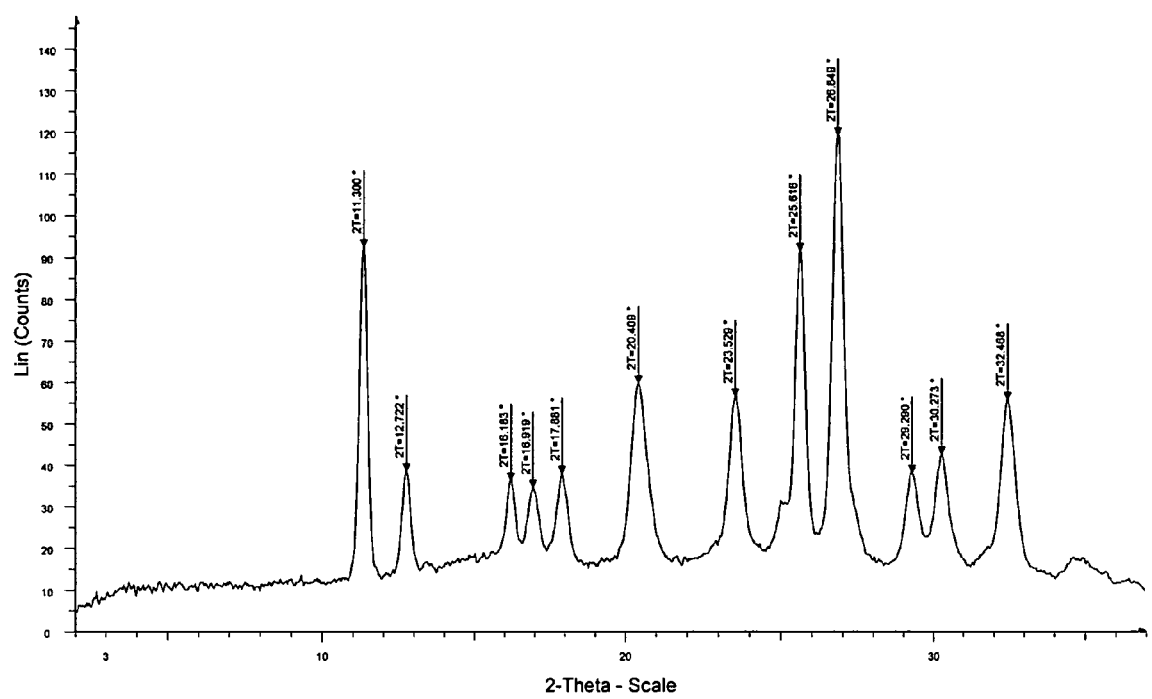
FIG. 26 shows a PXRD diffractogram of a 1:0.2:0.8 urea:5-fluorouracil:uracil mixed co-crystal.
Figure 27:
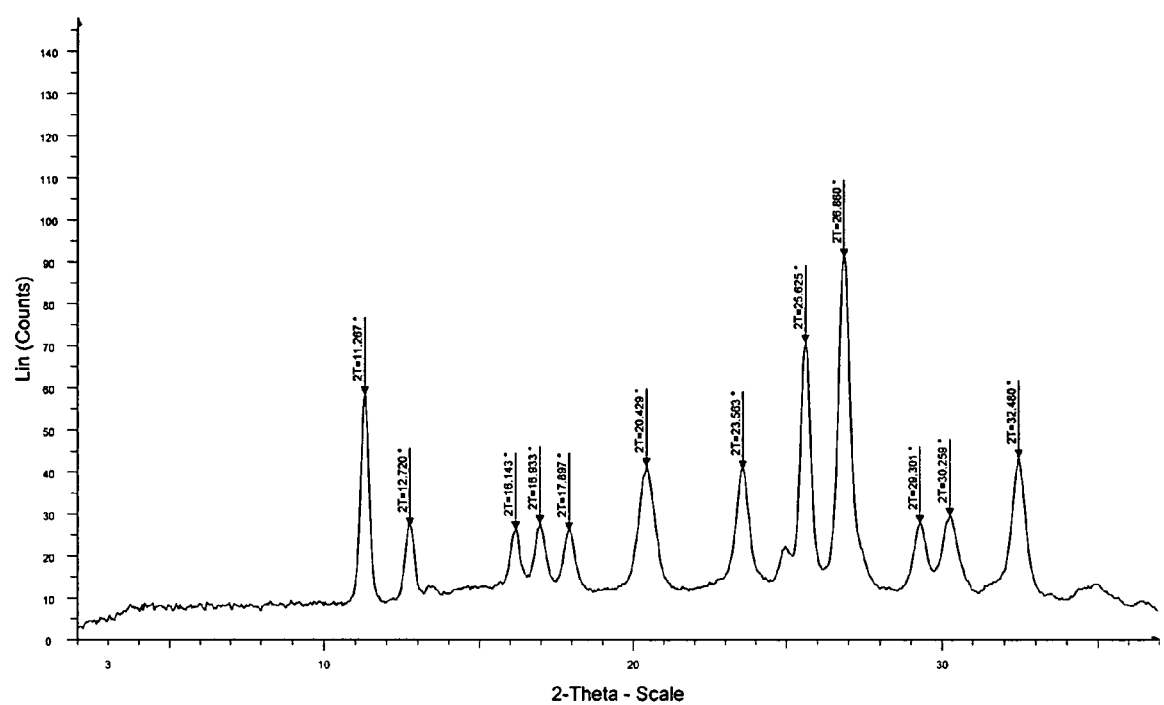
FIG. 27 shows a PXRD diffractogram of a 1:0.3:0.7 urea:5-fluorouracil:uracil mixed co-crystal.
Figure 28:
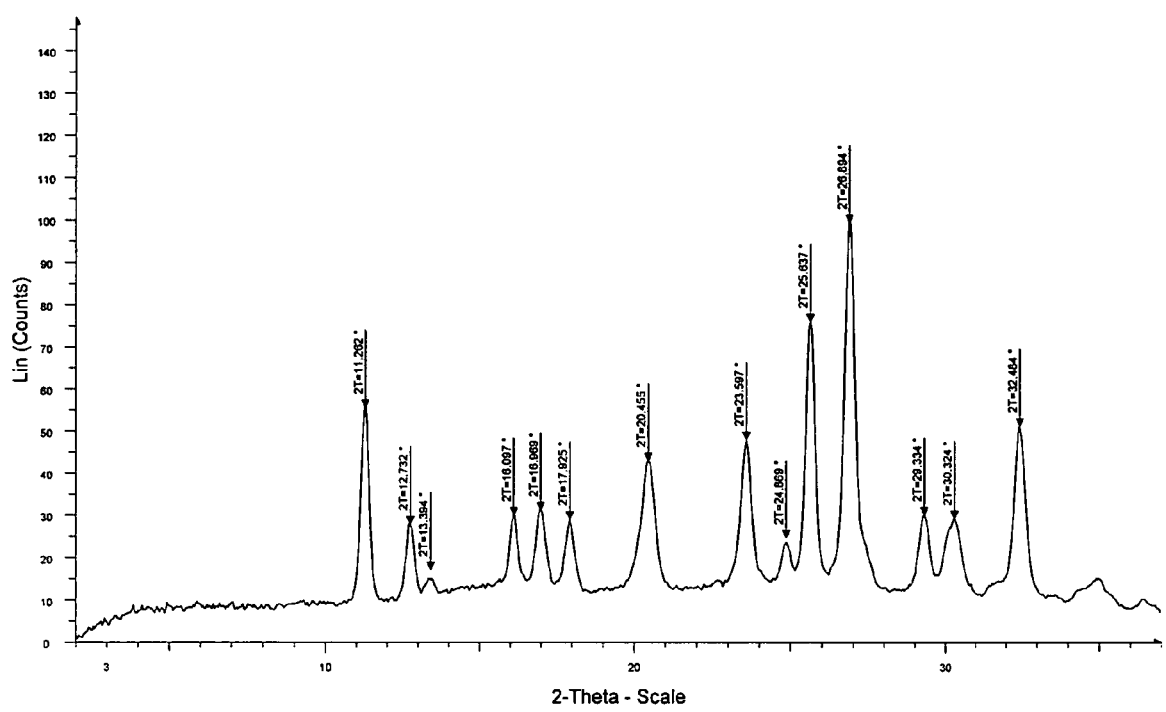
FIG. 28 shows a PXRD diffractogram of a 1:0.4:0.6 urea:5-fluorouracil:uracil mixed co-crystal.
Figure 29:
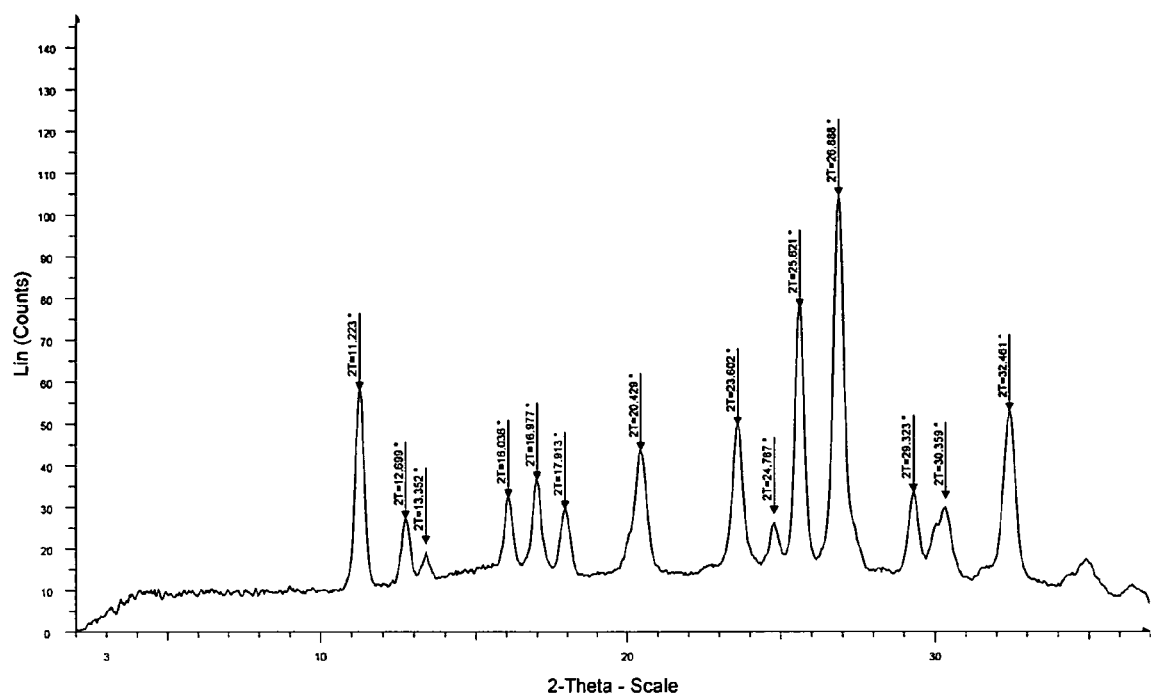
FIG. 29 shows a PXRD diffractogram of a 1:0.5:0.5 urea:5-fluorouracil:uracil mixed co-crystal.
Figure 30:
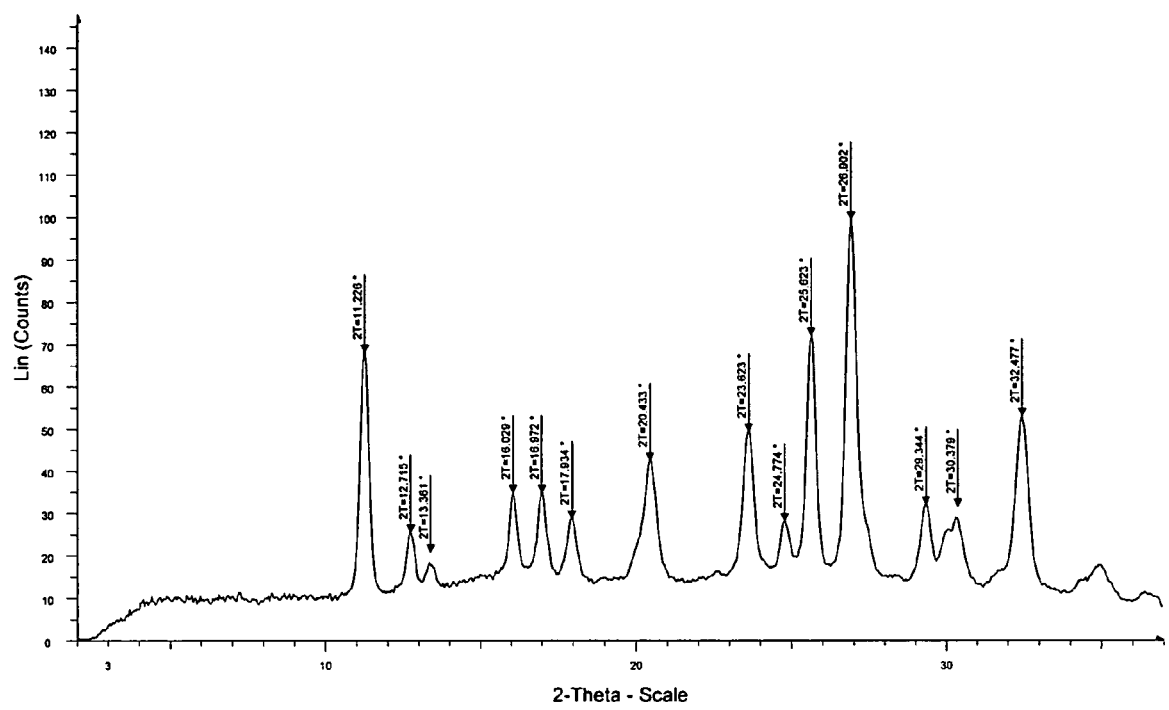
FIG. 30 shows a PXRD diffractogram of a 1:0.6:0.4 urea:5-fluorouracil:uracil mixed co-crystal.
Figure 31:
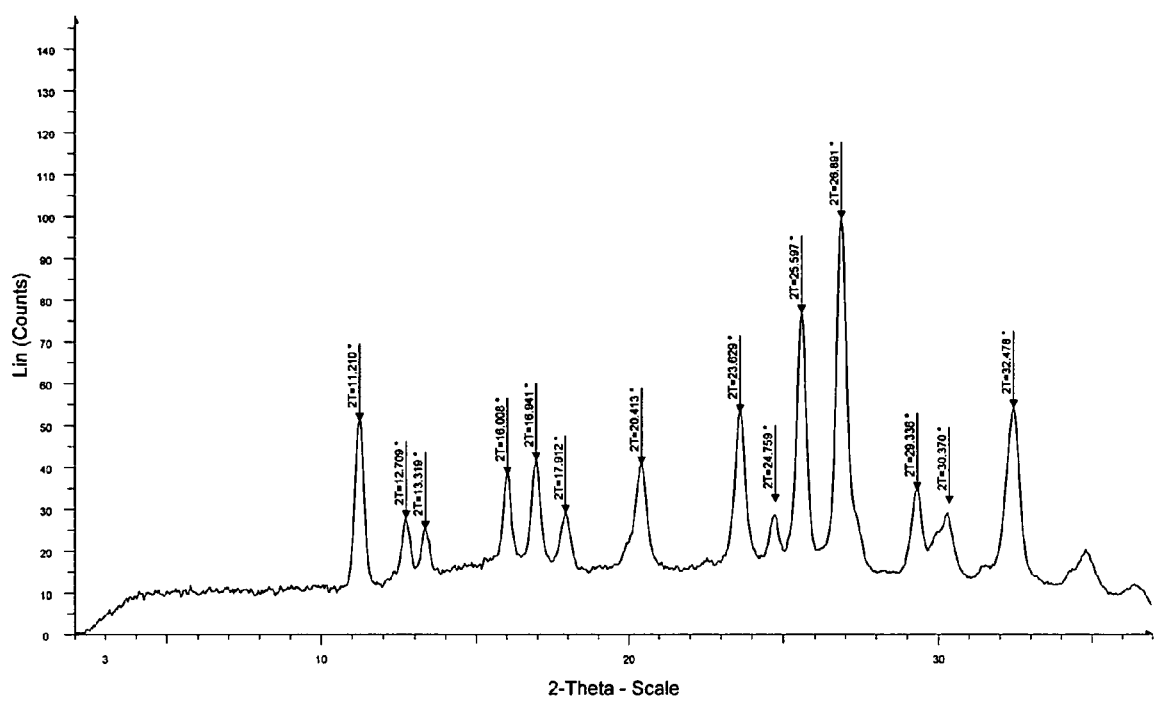
FIG. 31 shows a PXRD diffractogram of a 1:0.7:0.3 urea:5-fluorouracil:uracil mixed co-crystal.
Figure 32:
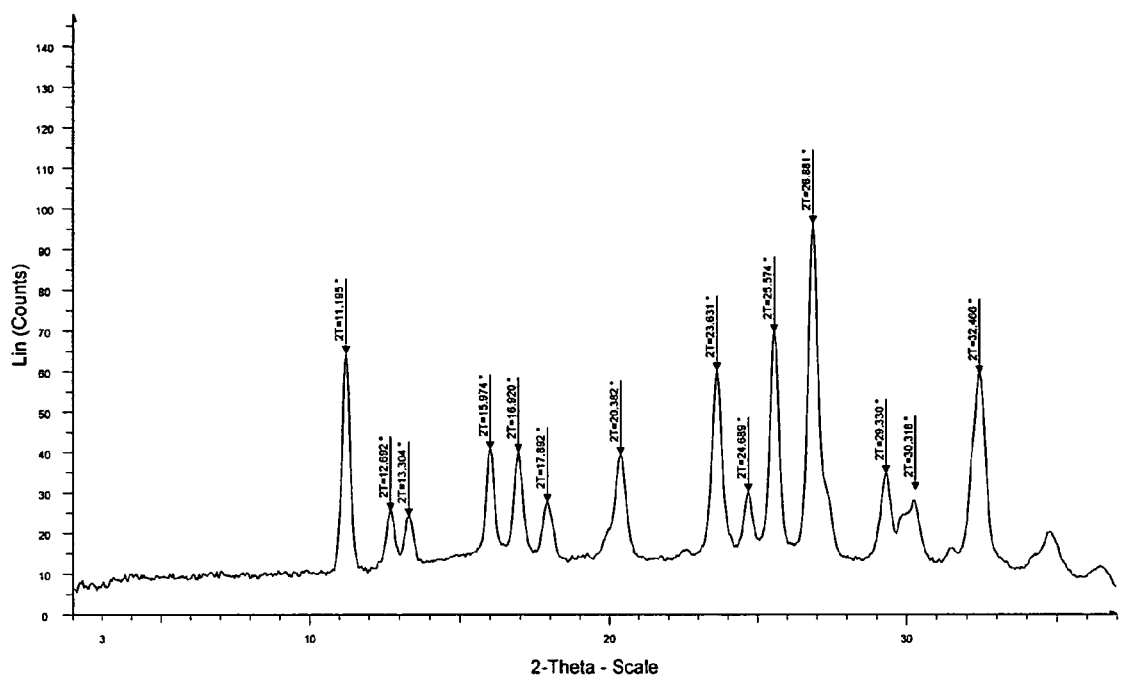
FIG. 32 shows a PXRD diffractogram of a 1:0.8:0.2 urea:5-fluorouracil:uracil mixed co-crystal.
Figure 33:
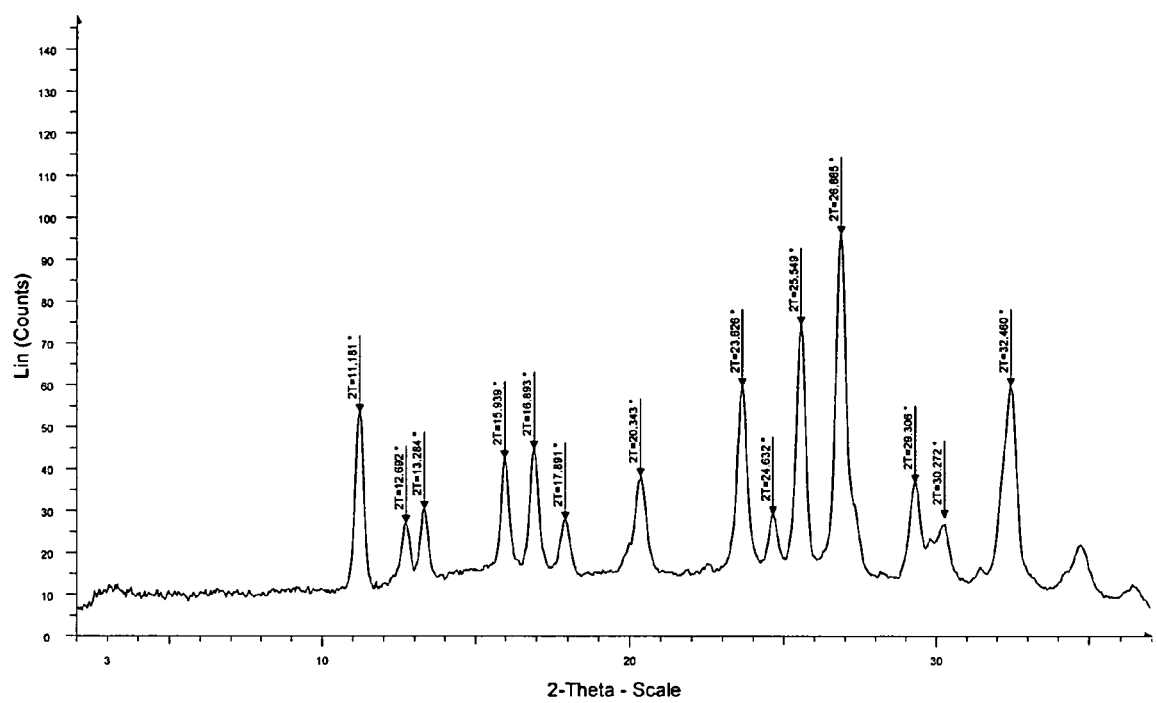
FIG. 33 shows a PXRD diffractogram of a 1:0.9:0.1 urea:5-fluorouracil:uracil mixed co-crystal.
Figure 34:
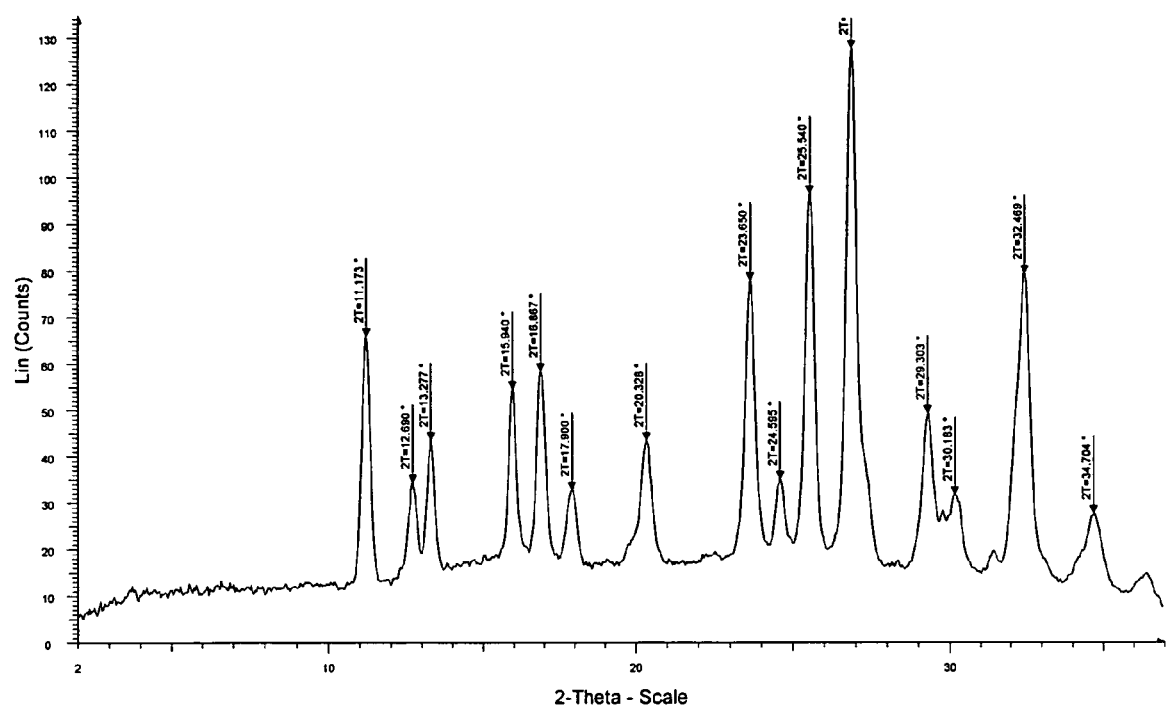
FIG. 34 shows a PXRD diffractogram of the urea:5-fluorouracil parent co-crystal.

The mixed co-crystals were evaluated using DSC. FIG. 23 represents a plot of the endotherms observed in the mixed co-crystals versus % composition. (FIG. 23 shows mixed co-crystals as a percent composition of 5-fluorouracil. 100 percent=all 5-fluorouracil co-crystal former, 50 percent=50 percent uracil co-crystal former and 50 percent 5-fluorouracil co-crystal former, 0 percent=all uracil co-crystal former) The plot in FIG. 23 indicates that the endotherms (shown in degrees C.) of the mixed co-crystals increased as the amount of uracil decreased up to a maximum at the 50:50 mixture. The endotherms then decreased for mixtures containing from 60% 5-fluorouracil up to 100% 5-fluorouracil.

FIGS. 24-34 show PXRD diffractograms of the nine urea mixed co-crystals and both parent co-crystals described above. The 1:1 urea:uracil co-crystal can be characterized by any one, any two, any three, any four, any five, or any six or more of the peaks in FIG. 24 including, but not limited to, 11.35, 12.72, 16.25, 16.91, 17.87, 20.43, 23.53, 25.64, 26.84, 29.25, 30.29, and 32.42 degrees 2-theta (Bruker, as collected). The 1:0.1:0.9 urea:5-fluorouracil:uracil mixed co-crystal can be characterized by any one, any two, any three, any four, any five, or any six or more of the peaks in FIG. 25 including, but not limited to, 11.32, 12.70, 16.19, 16.90, 17.87, 20.40, 23.51, 25.61, 26.82, 29.25, 30.29, and 32.43 degrees 2-theta (Bruker, as collected). The 1:0.2:0.8 urea:5-fluorouracil:uracil mixed co-crystal can be characterized by any one, any two, any three, any four, any five, or any six or more of the peaks in FIG. 26 including, but not limited to, 11.30, 12.72, 16.18, 16.92, 17.88, 20.41, 23.53, 25.62, 26.85, 29.29, 30.27, and 32.47 degrees 2-theta (Bruker, as collected). The 1:0.3:0.7 urea:5-fluorouracil:uracil mixed co-crystal can be characterized by any one, any two, any three, any four, any five, or any six or more of the peaks in FIG. 27 including, but not limited to, 11.27, 12.72, 16.14, 16.93, 17.90, 20.43, 23.56, 25.63, 26.86, 29.30, 30.26, and 32.48 degrees 2-theta (Bruker, as collected). The 1:0.4:0.6 urea:5-fluorouracil:uracil mixed co-crystal can be characterized by any one, any two, any three, any four, any five, or any six or more of the peaks in FIG. 28 including, but not limited to, 11.26, 12.73, 13.39, 16.10, 16.97, 17.93, 20.46, 23.60, 24.87, 25.64, 26.89, 29.33, 30.32, and 32.48 degrees 2-theta (Bruker, as collected). The 1:0.5:0.5 urea:5-fluorouracil:uracil mixed co-crystal can be characterized by any one, any two, any three, any four, any five, or any six or more of the peaks in FIG. 29 including, but not limited to, 11.22, 12.70, 13.35, 16.04, 16.98, 17.91, 20.43, 23.60, 24.79, 25.62, 26.89, 29.32, 30.36, and 32.46 degrees 2-theta (Bruker, as collected). The 1:0.6:0.4 urea:5-fluorouracil:uracil mixed co-crystal can be characterized by any one, any two, any three, any four, any five, or any six or more of the peaks in FIG. 30 including, but not limited to, 11.23, 12.72, 13.36, 16.03, 16.97, 17.93, 20.43, 23.62, 24.77, 25.62, 26.90, 29.34, 30.38, and 32.48 degrees 2-theta (Bruker, as collected). The 1:0.7:0.3 urea:5-fluorouracil:uracil mixed co-crystal can be characterized by any one, any two, any three, any four, any five, or any six or more of the peaks in FIG. 31 including, but not limited to, 11.21, 12.71, 13.32, 16.01, 16.94, 17.91, 20.41, 23.63, 24.76, 25.60, 26.89, 29.34, 30.37, and 32.48 degrees 2-theta (Bruker, as collected). The 1:0.8:0.2 urea:5-fluorouracil:uracil mixed co-crystal can be characterized by any one, any two, any three, any four, any five, or any six or more of the peaks in FIG. 32 including, but not limited to, 11.20, 12.69, 13.30, 15.97, 16.92, 17.89, 20.38, 23.63, 24.69, 25.57, 26.88, 29.33, 30.32, and 32.47 degrees 2-theta (Bruker, as collected). The 1:0.9:0.1 urea:5-fluorouracil:uracil mixed co-crystal can be characterized by any one, any two, any three, any four, any five, or any six or more of the peaks in FIG. 33 including, but not limited to, 11.18, 12.69, 13.28, 15.94, 16.89, 17.89, 20.34, 23.63, 24.63, 25.55, 26.87, 29.31, 30.27, and 32.46 degrees 2-theta (Bruker, as collected). The 1:1 urea:5-fluorouracil co-crystal can be characterized by any one, any two, any three, any four, any five, or any six or more of the peaks in FIG. 34 including, but not limited to, 11.17, 12.69, 13.28, 15.94, 16.87, 17.90, 20.33, 23.65, 24.60, 25.54, 26.85, 29.30, 30.18, and 32.47 degrees 2-theta (Bruker, as collected).

What is claimed is:

1. A mixed co-crystal, comprising:
   (a) urea;
   (b) a first co-crystal former; and
   (c) a second co-crystal former which is isomorphically substitutable with said first co-crystal former,
   wherein said first and second co-crystal formers are distributed homogenously or randomly throughout the co-crystal,
   and wherein both the said first and second co-crystal formers are selected from one of the groups of isomorphs consisting of:
   phenylalanine, tyrosine, cinnamic acid, hippuric acid, procaine, resveratrol, tryptophan,
   5-fluorouracil and uracil.

2. The mixed co-crystal according to claim 1, further comprising a third co-crystal former which is isomorphically substitutable with said first co-crystal former.

* * * * *